(12) United States Patent
Imamura et al.

(10) Patent No.: US 6,518,045 B1
(45) Date of Patent: Feb. 11, 2003

(54) FELINE CYTOKINE PROTEIN

(75) Inventors: Takayuki Imamura, Kumamoto (JP); Hiroaki Maeda, Kumamoto (JP); Takeshi Fujiyasu, Kumamoto (JP); Yoshitaka Imagawa, Kumamoto (JP); Sachio Tokiyoshi, Kumamoto (JP)

(73) Assignee: Juridical Foundation The Chemo-Sero-Therapeutic Research Institute, Kumamoto-ken (JP)

( * ) Notice: Subject to any disclaimer, the term of this patent is extended or adjusted under 35 U.S.C. 154(b) by 0 days.

(21) Appl. No.: 09/302,495

(22) Filed: Apr. 30, 1999

Related U.S. Application Data

(62) Division of application No. 09/011,143, filed as application No. PCT/JP97/01824 on May 29, 1997.

(30) Foreign Application Priority Data

Jun. 4, 1996 (JP) .............................................. 8-165249

(51) Int. Cl.⁷ ................................................ C12P 21/04
(52) U.S. Cl. ................. 435/69.52; 536/23.5; 424/185.1
(58) Field of Search ..................... 424/185.1; 536/23.5; 435/252.3, 69.1, 69.3, 69.5, 69.52; 530/350

(56) References Cited

FOREIGN PATENT DOCUMENTS

| EP | 0433827 A2 | 6/1991 |
| EP | 0640689 A2 | 3/1995 |

OTHER PUBLICATIONS

Fehr et al., Nucleotide and predicted peptide sequence of feline interleukin–12 (IL–12), *The Journal of Sequencing and Mapping*, 8(1–2)77–82 (1997).

Rottman et al., "A reverse transcription–polymerase chain reaction technique to detect feline cytokine genes", *Veterinary Immunology and Immunopathology*, 45:1–18 (1995).

Zarlenga et al., "Enzymatic amplification and molecular cloning of cDNA encoding the small and large subunits of bovine interleukin 12", *Biochemica et Biophysica. Acta.*, 1270:215–217 (1995).

Bush et al, "Moleccular cloning of feline interleukin 12 p35 reveals the conservation of leucine–zipper motifs present in human and murine IL–12 p35", *Molecular Immunology* 31(17):1373–1374 (1994).

Chizzonite et al, "IL–12: Monoclonal antibodies specificc for the 40–kDa subunit block receptor binding biologic activity on activated human lymphoblasts", *J. Immunology* 147(5):1548–1556 (1991).

Germann et al, "The IL–12 p40 homodimer as a speccific antagonist of the IL–12 heterodimer", *Immunology Today* 16(10):500–501 (1995).

Neurath et al, "Antibodies to inerleukin 12 abrogate established experimental colitis in mice", *J. Exp. Med.* 182:1281–1290 (1995).

Schijins et al, "Molecualr cloning of cat interleukin–12", *Immunogenetics* 45:462–463 (1997).

Schoenhaut et al, "Cloning and expression of murine IL–12", *J. Immunol.* 148(11):3433–3440 (1992).

Trinchieri, "Interleukin–12: A proinflammatory cytokine with immunoregulatory functions that bridge innate resistance and antigen–specific adaptive immunity", *Annu. Rev. Immunol.* 13:251–276 (1995).

Wen et al, "Erythropoietin structure–function relationshiips: High degree of sequence homolgy among mammals", *Blood* 82(5):1507–1516 (1993).

Wolf et al, "Cloning if cDNA for natural killer cell stimulatory factor, a heterodimeric cytokine with multiple bilogic effects on T and natural killer cells", *J. Immunol.* 146(9):3074–3081 (1991).

Yamamoto et al, "A feline retrovirus induced T–lymphoblastoid cell–line that produces an atypical alpha type of interferon", *Veterinary Immunology and Immunopathology* 11:1–19 (1986).

*Primary Examiner*—Laurie Scheiner
(74) *Attorney, Agent, or Firm*—Browdy and Neimark, PLLC

(57) ABSTRACT

A novel feline cytokine protein having the activity to enhance the cytotoxic activity of feline cytotoxic T lymphocytes, a DNA sequence coding for said protein, a recombinant DNA for expressing said protein, an expression vector comprising said recombinant DNA, a transformant which is transformed with said expression vector, a process for preparing said protein by culturing said transformant, and an antibody against said protein are provided. The novel feline cytokine protein of the present invention is a heterologous dimer comprising FLAF p35 and FLAF p40 and can be used for treating feline infectious diseases such as feline herpes virus type 1 (FHV-1) or feline calicivirus (FCV).

17 Claims, 19 Drawing Sheets

Fig. 9

| | | |
|---|---|---|
| Nucleotide sequence of clone 12 | CAA GGG GTG ACT TGT <u>GGA GCA GCG ACA CTC TCA GCA GAG AAG</u> | 600 |
| Amino acid sequence of clone 12 | Gln Gly Val Thr Cys Gly Ala Ala Thr Leu Ser Ala Glu Lys<br>144 | |
| Nucleotide sequence of clone 25 | <u>GA GCA GCG ACA CTC TCA GCA GAG AAG</u> | 600 |
| Amino acid sequence of clone 25 | Ala Ala Thr Leu Ser Ala Glu Lys<br>150 | |

```
                         SalI Site
                         GTC GAC
Nucleotide sequence of
      clone 12           GTC AGA GTG GA                                        612
Amino acid sequence of   Val Arg Val
      clone 12           160

SalI Site
                         GTC GAC
Nucleotide sequence of
      clone 25           GTC AGA GTG GAC AAC AGG GAT TAT AAG AAG TAC ACA GTG GAG  660
Amino acid sequence of   Val Arg Val Asp Asn Arg Asp Tyr Lys Lys Tyr Thr Val Glu
      clone 25           158
```

Negative control CAGp40  Negative control CAGp40

Protein staining  Western blotting

Fig. 13

| | | |
|---|---|---|
| Nucleotide sequence of clone 20 | ATG TGC CCG CCG CGT GGC CTC CTC CTT GTA ACC ATC | 179 |
| Amino acid sequence of clone 20 | Met Cys Pro Pro Arg Gly Leu Leu Leu Val Thr Ile<br>-25 | |
| Feline IL12p35 | \* \* \* \* Leu Cys \* \* \* \* \* \* | |

| | | |
|---|---|---|
| Nucleotide sequence of clone 20 | CTG GTC CTG TTA AAC CAC CTG GAC CAC CTC AGT TTG | 215 |
| Amino acid sequence of clone 20 | Leu Val Leu Leu [Asn His Leu] Asp His Leu Ser Leu<br>-13 | |
| Feline IL12p35 | \* \* \* \*         \* \* \* \* \* | |

| | | |
|---|---|---|
| Nucleotide sequence of clone 20 | ATA CTT CTT CAT GCT TTC AGA ATT CGT GCA GTG ACC ATC AAT | 780 |
| Amino acid sequence of clone 20 | Ile Leu Leu His [Ala Phe Arg Ile Arg Ala Val Thr Ile Asn<br>175 | |
| Feline IL12p35 | \* \* \* \* | |

| | | |
|---|---|---|
| Nucleotide sequence of clone 20 | AGA ATG ATG AGC TAC CTG AAT TCT TCC TAA | 810 |
| Amino acid sequence of clone 20 | Arg Met Met Ser Tyr Leu Asn Ser Ser]<br>189 | |

Fig. 16
 
Purified FLAF (protein staining)    Purified FLAF (Western blotting)

Purified FLAF

SEQUENCE LISTING (1) GENERAL INFORMATION:

(iii) NUMBER OF SEQUENCES: 26

(2) INFORMATION FOR SEQ ID NO: 1:

(i) SEQUENCE CHARACTERISTICS:
      (A) LENGTH: 329 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO: 1:

```
Met His Pro Gln Gln Leu Val Ile Ala Trp Phe Tyr Leu Val Leu Leu
1               5                   10                  15

Ala Pro Pro Leu Met Ala Ile Trp Glu Leu Glu Lys Asn Val Tyr Val
            20                  25                  30

Val Glu Leu Asp Trp His Pro Asp Ala Pro Gly Glu Met Val Val Leu
        35                  40                  45

Thr Cys Asn Thr Pro Glu Glu Asp Asp Ile Thr Trp Thr Ser Asp Gln
    50                  55                  60

Ser Ser Glu Val Leu Gly Ser Gly Lys Thr Leu Thr Ile Gln Val Lys
65                  70                  75                  80

Glu Phe Ala Asp Ala Gly Gln Tyr Thr Cys His Lys Gly Gly Glu Val
                85                  90                  95

Leu Ser His Ser Phe Leu Leu Ile His Lys Lys Glu Asp Gly Ile Trp
            100                 105                 110

Ser Thr Asp Ile Leu Arg Glu Gln Lys Glu Ser Lys Asn Lys Ile Phe
        115                 120                 125

Leu Lys Cys Glu Ala Lys Asn Tyr Ser Gly Arg Phe Thr Cys Trp Trp
```

```
        130                 135                 140
Leu Thr Ala Ile Ser Thr Asp Leu Lys Phe Thr Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Lys Val Arg Val Asp Asn Arg Asp Tyr Lys Lys Tyr Thr Val
                180                 185                 190

Glu Cys Gln Glu Gly Ser Ala Cys Pro Ala Ala Glu Glu Ser Leu Pro
                195                 200                 205

Ile Glu Val Val Asp Ala Ile His Lys Leu Lys Tyr Glu Asn Tyr
                210                 215                 220

Thr Ser Ser Phe Phe Ile Arg Asp Ile Ile Lys Pro Asp Pro Pro Lys
225                 230                 235                 240

Asn Leu Gln Leu Lys Pro Leu Lys Asn Ser Arg His Val Glu Val Ser
                245                 250                 255

Trp Glu Tyr Pro Asp Thr Trp Ser Thr Pro His Ser Tyr Phe Ser Leu
                260                 265                 270

Thr Phe Gly Val Gln Val Gln Gly Lys Asn Asn Arg Glu Lys Lys Asp
                275                 280                 285

Arg Leu Ser Val Asp Lys Thr Ser Ala Lys Val Val Cys His Lys Asp
290                 295                 300

Ala Lys Ile Arg Val Gln Ala Arg Asp Arg Tyr Tyr Ser Ser Ser Trp
305                 310                 315                 320

Ser Asn Trp Ala Ser Val Ser Cys Ser
                325

(2) INFORMATION FOR SEQ ID NO: 2:

(i) SEQUENCE CHARACTERISTICS:
        (A) LENGTH: 307 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 2:

Ile Trp Glu Leu Glu Lys Asn Val Tyr Val Val Glu Leu Asp Trp His
1                   5                  10                  15

Pro Asp Ala Pro Gly Glu Met Val Val Leu Thr Cys Asn Thr Pro Glu
                20                  25                  30

Glu Asp Asp Ile Thr Trp Thr Ser Asp Gln Ser Ser Glu Val Leu Gly
                35                  40                  45

Ser Gly Lys Thr Leu Thr Ile Gln Val Lys Glu Phe Ala Asp Ala Gly
50                  55                  60

Gln Tyr Thr Cys His Lys Gly Gly Glu Val Leu Ser His Ser Phe Leu
65                  70                  75                  80

Leu Ile His Lys Lys Glu Asp Gly Ile Trp Ser Thr Asp Ile Leu Arg
                85                  90                  95

Glu Gln Lys Glu Ser Lys Asn Lys Ile Phe Leu Lys Cys Glu Ala Lys
                100                 105                 110

Asn Tyr Ser Gly Arg Phe Thr Cys Trp Trp Leu Thr Ala Ile Ser Thr
                115                 120                 125

Asp Leu Lys Phe Thr Val Lys Ser Ser Arg Gly Ser Ser Asp Pro Gln
                130                 135                 140

Gly Val Thr Cys Gly Ala Ala Thr Leu Ser Ala Glu Lys Val Arg Val
```

```
145                 150                 155                 160
Asp Asn Arg Asp Tyr Lys Lys Tyr Thr Val Glu Cys Gln Glu Gly Ser
                165                 170                 175

Ala Cys Pro Ala Ala Glu Glu Ser Leu Pro Ile Glu Val Val Val Asp
            180                 185                 190

Ala Ile His Lys Leu Lys Tyr Glu Asn Tyr Thr Ser Ser Phe Phe Ile
            195                 200                 205

Arg Asp Ile Ile Lys Pro Asp Pro Pro Lys Asn Leu Gln Leu Lys Pro
        210                 215                 220

Leu Lys Asn Ser Arg His Val Glu Val Ser Trp Glu Tyr Pro Asp Thr
225                 230                 235                 240

Trp Ser Thr Pro His Ser Tyr Phe Ser Leu Thr Phe Gly Val Gln Val
                245                 250                 255

Gln Gly Lys Asn Asn Arg Glu Lys Lys Asp Arg Leu Ser Val Asp Lys
            260                 265                 270

Thr Ser Ala Lys Val Val Cys His Lys Asp Ala Lys Ile Arg Val Gln
        275                 280                 285

Ala Arg Asp Arg Tyr Tyr Ser Ser Ser Trp Ser Asn Trp Ala Ser Val
    290                 295                 300

Ser Cys Ser
305

(2) INFORMATION FOR SEQ ID NO: 3:

(i) SEQUENCE CHARACTERISTICS:
        (A) LENGTH: 222 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 3:

Met Cys Pro Pro Arg Gly Leu Leu Val Thr Ile Leu Val Leu Leu
1               5                   10                  15

Asn His Leu Asp His Leu Ser Leu Ala Arg Asn Leu Pro Thr Pro Thr
                20                  25                  30

Pro Ser Pro Gly Met Phe Gln Cys Leu Asn His Ser Gln Thr Leu Leu
            35                  40                  45

Arg Ala Ile Ser Asn Thr Leu Gln Lys Ala Arg Gln Thr Leu Glu Phe
        50                  55                  60

Tyr Ser Cys Thr Ser Glu Glu Ile Asp His Glu Asp Ile Thr Lys Asp
65                  70                  75                  80

Lys Thr Ser Thr Val Glu Ala Cys Leu Pro Leu Glu Leu Thr Met Asn
                85                  90                  95

Glu Ser Cys Leu Ala Ser Arg Glu Ile Ser Leu Ile Thr Asn Gly Ser
            100                 105                 110

Cys Leu Ala Ser Arg Lys Thr Ser Phe Met Thr Thr Leu Cys Leu Ser
            115                 120                 125

Ser Ile Tyr Glu Asp Leu Lys Met Tyr Gln Val Glu Phe Lys Ala Met
        130                 135                 140

Asn Ala Lys Leu Leu Met Asp Pro Lys Arg Gln Ile Phe Leu Asp Gln
145                 150                 155                 160

Asn Met Leu Thr Ala Ile Asp Glu Leu Leu Gln Ala Leu Asn Val Asn
                165                 170                 175

Ser Val Thr Val Pro Gln Asn Ser Ser Leu Glu Glu Pro Asp Phe Tyr
```

```
                      180                 185                 190
Lys Thr Lys Ile Lys Leu Cys Ile Leu Leu His Ala Phe Arg Ile Arg
            195                 200                 205
Ala Val Thr Ile Asn Arg Met Met Ser Tyr Leu Asn Ser Ser
            210                 215                 220
```

(2) INFORMATION FOR SEQ ID NO: 4:

(i) SEQUENCE CHARACTERISTICS:
        (A) LENGTH: 197 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 4:

```
Arg Asn Leu Pro Thr Pro Thr Pro Ser Pro Gly Met Phe Gln Cys Leu
1               5                   10                  15
Asn His Ser Gln Thr Leu Leu Arg Ala Ile Ser Asn Thr Leu Gln Lys
            20                  25                  30
Ala Arg Gln Thr Leu Glu Phe Tyr Ser Cys Thr Ser Glu Glu Ile Asp
        35                  40                  45
His Glu Asp Ile Thr Lys Asp Lys Thr Ser Thr Val Glu Ala Cys Leu
    50                  55                  60
Pro Leu Glu Leu Thr Met Asn Glu Ser Cys Leu Ala Ser Arg Glu Ile
65                  70                  75                  80
Ser Leu Ile Thr Asn Gly Ser Cys Leu Ala Ser Arg Lys Thr Ser Phe
                85                  90                  95
Met Thr Thr Leu Cys Leu Ser Ser Ile Tyr Glu Asp Leu Lys Met Tyr
            100                 105                 110
Gln Val Glu Phe Lys Ala Met Asn Ala Lys Leu Leu Met Asp Pro Lys
        115                 120                 125
Arg Gln Ile Phe Leu Asp Gln Asn Met Leu Thr Ala Ile Asp Glu Leu
    130                 135                 140
Leu Gln Ala Leu Asn Val Asn Ser Val Thr Val Pro Gln Asn Ser Ser
145                 150                 155                 160
Leu Glu Glu Pro Asp Phe Tyr Lys Thr Lys Ile Lys Leu Cys Ile Leu
                165                 170                 175
Leu His Ala Phe Arg Ile Arg Ala Val Thr Ile Asn Arg Met Met Ser
            180                 185                 190
Tyr Leu Asn Ser Ser
            195
```

(2) INFORMATION FOR SEQ ID NO: 5:

(i) SEQUENCE CHARACTERISTICS:
        (A) LENGTH: 2193 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 5:

```
AGCACGAGAG CAGAAGAGAC TAGTTTCAGA CCCAGAAAAC TCTGCAGCCT GCCCAGAAGC      60

AAGATGCATC CTCAGCAGCT GGTCATCGCC TGGTTTTACC TGGTTTTGCT GGCACCTCCT     120

CTCATGGCCA TATGGGAACT GGAGAAAAAC GTTTATGTTG TAGAGTTGGA CTGGCACCCT     180
```

```
GATGCCCCG GAGAAATGGT GGTCCTCACC TGCAATACTC CTGAAGAAGA TGACATCACC      240

TGGACCTCTG ACCAGAGCAG TGAAGTCCTA GGCTCTGGTA AAACTCTGAC CATCCAAGTC      300

AAAGAATTTG CAGATGCTGG CCAGTATACC TGTCATAAAG GAGGCGAGGT TCTGAGCCAT      360

TCGTTCCTCC TGATACACAA AAAGGAAGAT GGAATTTGGT CCACTGATAT CTTAAGGGAA      420

CAGAAAGAAT CCAAAAATAA GATCTTTCTA AATGTGAGG CAAAGAATTA TTCTGGACGT       480

TTCACCTGCT GGTGGCTGAC GGCAATCAGT ACCGATTTGA AATTCACTGT CAAAAGCAGC      540

AGAGGCTCCT CTGACCCCCA AGGGGTGACT TGTGGAGCAG CGACACTCTC AGCAGAGAAG      600

GTCAGAGTGG ACAACAGGGA TTATAAGAAG TACACAGTGG AGTGTCAGGA GGGCAGTGCC      660

TGCCCGGCTG CCGAGGAGAG CCTACCCATT GAAGTCGTGG TGGACGCTAT TCACAAGCTC      720

AAGTACGAAA ACTACACCAG CAGCTTCTTC ATCAGGGACA TCATCAAACC GGACCCACCC      780

AAGAACCTGC AACTGAAGCC ATTAAAAAAT TCTCGGCATG TGGAAGTGAG CTGGGAATAC      840

CCTGACACCT GGAGCACCCC ACATTCCTAC TTCTCCTTAA CATTTGGCGT ACAGGTCCAG      900

GGCAAGAACA ACAGAGAAAA GAAAGACAGA CTCTCCGTGG ACAAGACCTC AGCCAAGGTC      960

GTGTGCCACA AGGATGCCAA GATCCGCGTG CAAGCCAGAG ACCGCTACTA TAGCTCATCC     1020

TGGAGCAACT GGGCATCCGT GTCCTGCAGT TAGGTTCCAA TCCCAGGATG AAACCTTGGA     1080

GGAAAAGTGG AAGATATTAT GCAGAAGTTT TTAAAGAGAC AATGGAATAG GCCCCAAAAG     1140

TTATTTTCTA CCTAATTTGC TTTTTGCAAA GGATCATTAT AATGTTTTTG TAGTAGTTTT     1200

ACATTGAAAT GCCAAATGCC CACTGAAGCA ATTAGCTACT TTATTTATAG ATTTTCTAGC     1260

TAGCAGGTTG CCACCGACCT TAATGCTATT TAAATATTTA AGTAATTTAT GTATTTATTA     1320

ATTTATTGTT ATTGAACACT TCTGTGTCAA GATGTATTGT ATGTTCATAC TCTCAGGACC     1380

TGATCTGTAA GGAATAGGCC CTATTATGCA AAATGTGAAT TTATGTGTTA TTTATACTGA     1440

CAACTTTTCA AACAAGACTA CAAGTGCATC AGTTTTATGA CAACCAGTGA GAACACAGTA     1500

TTCTGATGCC AGCACCAATA ATATGTTTGT GATGGATGGG AACACAGTTA AACAGAAGCA     1560

CGGAGACATG AATCCATTTG AAAAGGTTCT GGTGACCGAG ATGTTAGCTC CTGTGTCCGT     1620

GAAGATTTCC TTGAGGTGGT GTTGCTAAAG CAATTCAGGA CCACCTGCAC TTCTAAGCAA     1680

GTTCAGTTGT TTTATTTTTG TTGTTGGTGG TGAGTTTTTT TGGGGGGAG GCAGTTGGAT      1740

GCCTGAATTT AGAAAGGACT AAAAAAATAA CTGAAATTGA AATTCAGCTT CAGCTACCCT     1800

GGCAGTCCCC ACCTCCATCT ATCTGTAAGA CATCGGAGAG TGACCCAGAG ACATTGGAAG     1860

TGTCTGGAAA GTAAAAAGGT CTTAGGATCC AAGAGGGAGA ACAAGTATAG TACGGCCAAG     1920

CAAACAAAAT TGTCAAAATT GCCAGCTGCT TTTTAATAGC CATGCAAGAC AACACAGAGT     1980

TGCAAAGAAA ACAATCAAGA ATTGCTTACT CATCAGCATG AGTGAACCTG ACTGGTGGAT     2040

ATGACCGGAC AGTGCCAATC ACTAAGGTGC TACTTTTAAG TAATGAATGT GCTTTCTGTA     2100

AAGTGATTTC ATTTGTTTTC TGTTTACTTA TTTCTGACAG TGAACTAATA AAAATATAAT     2160

TCTTCTTTGC AATAATAAAA AAAAAAAAAA AAA                                 2193

(2) INFORMATION FOR SEQ ID NO: 6:

(i) SEQUENCE CHARACTERISTICS:
        (A) LENGTH: 921 base pairs
        (B) TYPE: nucleic acid
        (C) STRANDEDNESS: single
        (D) TOPOLOGY: linear (ii) MOLECULE TYPE: cDNA
```

(xi) SEQUENCE DESCRIPTION: SEQ ID NO: 6:

```
ATATGGGAAC TGGAGAAAAA CGTTTATGTT GTAGAGTTGG ACTGGCACCC TGATGCCCCC      60
GGAGAAATGG TGGTCCTCAC CTGCAATACT CCTGAAGAAG ATGACATCAC CTGGACCTCT     120
GACCAGAGCA GTGAAGTCCT AGGCTCTGGT AAAACTCTGA CCATCCAAGT CAAAGAATTT     180
GCAGATGCTG GCCAGTATAC CTGTCATAAA GGAGGCGAGG TTCTGAGCCA TTCGTTCCTC     240
CTGATACACA AAAAGGAAGA TGGAATTTGG TCCACTGATA TCTTAAGGGA ACAGAAAGAA     300
TCCAAAAATA AGATCTTTCT AAAATGTGAG GCAAAGAATT ATTCTGGACG TTTCACCTGC     360
TGGTGGCTGA CGGCAATCAG TACCGATTTG AAATTCACTG TCAAAAGCAG CAGAGGCTCC     420
TCTGACCCCC AAGGGGTGAC TTGTGGAGCA GCGACACTCT CAGCAGAGAA GGTCAGAGTG     480
GACAACAGGG ATTATAAGAA GTACACAGTG GAGTGTCAGG AGGGCAGTGC CTGCCCGGCT     540
GCCGAGGAGA GCCTACCCAT TGAAGTCGTG GTGGACGCTA TTCACAAGCT CAAGTACGAA     600
AACTACACCA GCAGCTTCTT CATCAGGGAC ATCATCAAAC CGGACCCACC CAAGAACCTG     660
CAACTGAAGC CATTAAAAAA TTCTCGGCAT GTGGAAGTGA GCTGGGAATA CCCTGACACC     720
TGGAGCACCC CACATTCCTA CTTCTCCTTA ACATTTGGCG TACAGGTCCA GGGCAAGAAC     780
AACAGAGAAA AGAAAGACAG ACTCTCCGTG GACAAGACCT CAGCCAAGGT CGTGTGCCAC     840
AAGGATGCCA AGATCCGCGT GCAAGCCAGA GACCGCTACT ATAGCTCATC CTGGAGCAAC     900
TGGGCATCCG TGTCCTGCAG T                                              921
```

(2) INFORMATION FOR SEQ ID NO: 7:

(i) SEQUENCE CHARACTERISTICS:
        (A) LENGTH: 921 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 7:

```
ATATGGGAAC TGGAGAAAAA CGTTTATGTT GTAGAGTTGG ACTGGCACCC TGATGCCCCC      60
GGAGAAATGG TGGTCCTCAC CTGCAATACT CCTGAAGAAG ATGACATCAC CTGGACCTCT     120
GACCAGAGCA GTGAAGTCCT AGGCTCTGGT AAAACTCTGA CCATCCAAGT CAAAGAATTT     180
GCAGATGCTG GCCAGTATAC CTGTCATAAA GGAGGCGAGG TTCTGAGCCA TTCGTTCCTC     240
CTGATACACA AAAAGGAAGA TGGAATTTGG TCCACTGATA TCTTAAGGGA ACAGAAAGAA     300
TCCAAAAATA AGATCTTTCT AAAATGTGAG GCAAAGAATT ATTCTGGACG TTTCACCTGC     360
TGGTGGCTGA CGGCAATCAG TACCGATTTG AAATTCACTG TCAAAAGCAG CAGAGGCTCC     420
TCTGACCCCC AAGGGGTGAC TTGTGGAGCA GCGACACTCT CAGCAGAGAA GGTCAGAGTC     480
GACAACAGGG ATTATAAGAA GTACACAGTG GAGTGTCAGG AGGGCAGTGC CTGCCCGGCT     540
GCCGAGGAGA GCCTACCCAT TGAAGTCGTG GTGGACGCTA TTCACAAGCT CAAGTACGAA     600
AACTACACCA GCAGCTTCTT CATCAGGGAC ATCATCAAAC CGGACCCACC CAAGAACCTG     660
CAACTGAAGC CATTAAAAAA TTCTCGGCAT GTGGAAGTGA GCTGGGAATA CCCTGACACC     720
TGGAGCACCC CACATTCCTA CTTCTCCTTA ACATTTGGCG TACAGGTCCA GGGCAAGAAC     780
AACAGAGAAA AGAAAGACAG ACTCTCCGTG GACAAGACCT CAGCCAAGGT CGTGTGCCAC     840
AAGGATGCCA AGATCCGCGT GCAAGCCAGA GACCGCTACT ATAGCTCATC CTGGAGCAAC     900
TGGGCATCCG TGTCCTGCAG T                                              921
```

(2) INFORMATION FOR SEQ ID NO: 8:

(i) SEQUENCE CHARACTERISTICS:
        (A) LENGTH: 1441 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 8:

```
GGCACGAGGG AAAGTCCTGC CGCGCCTCGG GACAATTATA AAAATGTGAT CCCCTGGGTC      60
GGCTTCCCAC CATCGCCCTC ACCTGCTGCG TCCACCGTCC GGATCCAGCT CCAGCCCAGT     120
GTCCGCCCAG TGCCCGCTCA GCATGTGCCC GCCGCGTGGC CTCCTCCTTG TAACCATCCT     180
GGTCCTGTTA AACCACCTGG ACCACCTCAG TTTGGCCAGG AACCTCCCCA CACCCACACC     240
AAGCCCAGGA ATGTTCCAGT GCCTCAACCA CTCCCAAACC CTGCTGCGAG CCATCAGCAA     300
CACGCTTCAG AAGGCCAGAC AAACTCTAGA ATTTTACTCC TGCACTTCCG AAGAGATTGA     360
TCATGAAGAT ATCACAAAAG ATAAAACCAG CACAGTGGAG GCCTGCTTAC CACTGGAATT     420
AACCATGAAT GAGAGTTGCC TGGCTTCCAG AGAGATCTCT CTGATAACTA ATGGGAGTTG     480
CCTGGCCTCC AGAAAGACCT CTTTTATGAC GACCCTGTGC CTTAGCAGTA TCTATGAGGA     540
CTTGAAGATG TACCAGGTGG AGTTCAAGGC CATGAATGCA AAGCTGTTAA TGGATCCTAA     600
AAGGCAGATC TTTCTGGATC AAAACATGCT GACAGCTATT GATGAGCTGT ACAGGCCCT     660
GAATGTCAAC AGTGTGACTG TGCCACAGAA CTCCTCCCTG AAGAACCAG ATTTTTATAA     720
AACTAAAATC AAGCTCTGCA TACTTCTTCA TGCTTTCAGA ATTCGTGCAG TGACCATCAA     780
TAGAATGATG AGCTACCTGA ATTCTTCCTA AAAAGCTGAA GTCTCTCCCA ACCTTAAAGC     840
CACTTTTACA GAAATGTGAA CCAAAAAAAC AAACAAAAAC AAAACATATA TATATATATA     900
TATGTGTGTA TATATATATA TATATATATA TATATATATA TATATATATA TTTCATAGGA     960
TGTGGGTTAA GAACCAGGGA GTGGGTGGCT TGACCTGGTC CTCCTTAAGC TAGTACAATA    1020
ATTCTCATGC TTGTTTACAT TAGTTGCCAC CCAAAATTTG AAAGATATGA CTGTTATGTC    1080
CACATGATGC CTCTGACCAA GTCTATTTCA CATTTACTAG GGAGGGATAA GTTCTTTTTA    1140
AGTTTTCATG AGCAAATTGC TAAAGAGGGA AAATGTCCTT CCTTGAACAT GTTTTTCTTT    1200
TCCCTTTAAT AGAAAAGCAA GAATTTATAA GCTATTTCTG TACCTAAGTG TTTGTAGACA    1260
CAAACACCCC AGCATAATTT ATTTTAAAAT ACTTATTTAT ATAATTTTGT GTTCATGAAA    1320
GCATGTGAGC TAACTTATAT TTATTTATGT TATATTTATT AAAATATTTA TTATCCAATG    1380
GATTTGAGAA CTACCTTATT TTCTAAAAAT AAAATGATTG AATAAAAAAA AAAAAAAAA    1440
A                                                                    1441
```

(2) INFORMATION FOR SEQ ID NO: 9:

(i) SEQUENCE CHARACTERISTICS:
        (A) LENGTH: 591 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 9:

```
AGGAACCTCC CCACACCCAC ACCAAGCCCA GGAATGTTCC AGTGCCTCAA CCACTCCCAA      60
ACCCTGCTGC GAGCCATCAG CAACACGCTT CAGAAGGCCA GACAAACTCT AGAATTTTAC     120
```

```
TCCTGCACTT CCGAAGAGAT TGATCATGAA GATATCACAA AAGATAAAAC CAGCACAGTG        180

GAGGCCTGCT TACCACTGGA ATTAACCATG AATGAGAGTT GCCTGGCTTC CAGAGAGATC        240

TCTCTGATAA CTAATGGGAG TTGCCTGGCC TCCAGAAAGA CCTCTTTTAT GACGACCCTG        300

TGCCTTAGCA GTATCTATGA GGACTTGAAG ATGTACCAGG TGGAGTTCAA GGCCATGAAT        360

GCAAAGCTGT TAATGGATCC TAAAAGGCAG ATCTTTCTGG ATCAAAACAT GCTGACAGCT        420

ATTGATGAGC TGTTACAGGC CCTGAATGTC AACAGTGTGA CTGTGCCACA GAACTCCTCC        480

CTGGAAGAAC CAGATTTTTA TAAAACTAAA ATCAAGCTCT GCATACTTCT TCATGCTTTC        540

AGAATTCGTG CAGTGACCAT CAATAGAATG ATGAGCTACC TGAATTCTTC C                591
```

(2) INFORMATION FOR SEQ ID NO: 10:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 10:

```
Ala Phe Arg Ile Arg Ala Val Thr Ile Asn Arg Met Met Ser Tyr Leu
1               5                   10                  15

Asn Ser Ser
```

(2) INFORMATION FOR SEQ ID NO: 11:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 11:

```
Ile Trp Glu Leu Glu Lys Asn Val Tyr Val Val Glu Leu Asp Trp His
1               5                   10                  15

Pro Asp Ala Pro
            20
```

(2) INFORMATION FOR SEQ ID NO: 12:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 12:

```
ATCTGGGARC TSGARAARAA CGTSTACGTS GTSGARCT                                38
```

(2) INFORMATION FOR SEQ ID NO: 13:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 13:

GGGGTACCGT CGACTCTGAC CTTCTCTGCT GA                    32

(2) INFORMATION FOR SEQ ID NO: 14:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 14:

GCTCTAGAAA GCTTGAATTC GTCGACAACA GGGATTATAA GAAG        44

(2) INFORMATION FOR SEQ ID NO: 15:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 15:

ATGTGCCCNC CNCTNTGYCT N                                21

(2) INFORMATION FOR SEQ ID NO: 16:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 16:

ATGTGCCCNC CNTTRTGYTT R                                21

(2) INFORMATION FOR SEQ ID NO: 17:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 17:

RTGNAGNAGD ATGCANAGCT T                                21

(2) INFORMATION FOR SEQ ID NO: 18:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 18:

RTGYAAYAAD ATGCAYAACT T                                21

(2) INFORMATION FOR SEQ ID NO: 19:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 19:

Arg Asn Leu Pro Thr Pro Thr Pro Ser Pro
1               5                   10

(2) INFORMATION FOR SEQ ID NO: 20:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 20:

Thr Ser Glu Glu Ile Asp His Glu Asp Ile Thr Lys Asp Lys Thr Ser
1               5                   10                  15

Thr Val Glu Ala Cys
            20

(2) INFORMATION FOR SEQ ID NO: 21:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 21:

Ser Ser Leu Glu Glu Pro Asp Phe Tyr Lys Thr Lys Ile Lys Leu Cys
1               5                   10                  15

(2) INFORMATION FOR SEQ ID NO: 22:

(i) SEQUENCE CHARACTERISTICS:
        (A) LENGTH: 95 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 22:

CCGAGCTCGG GTCGACGGCC GCCGCCATGT GCCCCCCCCG TGGCCTCCTC CTGGTGACCA    60

TCCTGGTCCT GCTGAACCAC CTGGACCACC TCAGT                              95

(2) INFORMATION FOR SEQ ID NO: 23:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 23:

ACTAGTCTCG AGTTTTTTTT TTTTTTTTTT                                              30

(2) INFORMATION FOR SEQ ID NO: 24:

(i) SEQUENCE CHARACTERISTICS:
        (A) LENGTH: 79 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 24:

TGAAGATATC ACAAAAGATA AAACCAGCAC AGTGGAGGCC TGCCTGCCAC TGGAACTGAC              60

CATGAATGAG AGTTGCCTG                                                          79

(2) INFORMATION FOR SEQ ID NO: 25:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 25:

AGGATCCATC AGCAGCTTTG CATTCATGGC CTTGAA                                       36

(2) INFORMATION FOR SEQ ID NO: 26:

(i) SEQUENCE CHARACTERISTICS:
        (A) LENGTH: 689 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 26:

GCCGCCATGT GCCCCCCCCG TGGCCTCCTC CTGGTGACCA TCCTGGTCCT GCTGAACCAC              60

CTGGACCACC TCAGTTTGGC CAGGAACCTC CCCACACCCA CACCAAGCCC AGGAATGTTC             120

CAGTGCCTCA ACCACTCCCA AACCCTGCTG CGAGCCATCA GCAACACGCT TCAGAAGGCC             180

AGACAAACTC TAGAATTTTA CTCCTGCACT TCCGAAGAGA TTGATCATGA AGATATCACA             240

AAAGATAAAA CCAGCACAGT GGAGGCTGC CTGCCACTGG AACTGACCAT GAATGAGAGT              300

TGCCTGGCTT CCAGAGAGAT CTCTCTGATA ACTAATGGGA GTTGCCTGGC CTCCAGAAAG             360

ACCTCTTTTA TGACGACCCT GTGCCTTAGC AGTATCTATG AGGACTTGAA GATGTACCAG             420

GTGGAGTTCA AGGCCATGAA TGCAAAGCTG CTGATGGATC CTAAAAGGCA GATCTTTCTG             480

GATCAAAACA TGCTGACAGC TATTGATGAG CTGTTACAGG CCCTGAATGT CAACAGTGTG             540

ACTGTGCCAC AGAACTCCTC CCTGGAAGAA CCAGATTTTT ATAAAACTAA AATCAAGCTC             600

TGCATACTTC TTCATGCTTT CAGAATTCGT GCAGTGACCA TCAATAGAAT GATGAGCTAC             660

CTGAATTCTT CCTAAAAAGC TGAAGTCTC                                              689

FELINE CYTOKINE PROTEIN

This is a division of copending parent application Ser. No. 09/011,143, filed Feb. 4, 1998, which is a 371 of PCT/JP97/01824, filed May 29, 1997.

TECHNICAL FIELD

The present invention relates to a novel polypeptide, a novel protein comprising a homologous dimer or a heterologous dimer of said polypeptide, a novel DNA coding for said peptide, a recombinant DNA molecule comprising said DNA, a transformant which is transformed with said recombinant DNA molecule, an antibody against said novel polypeptide or said novel protein, a process for preparing said novel polypeptide or said novel protein, and an agent for treating feline viral diseases comprising said novel protein or said novel antibody. More particularly, the present invention relates to a feline cytokine protein comprising two distinct novel polypeptides having an activity to damage virus-infected cells by activating feline cytotoxic T lymphocytes and a gene coding for said cytokine protein as well as a process for preparing said feline cytokine protein.

BACKGROUND ART

A cat is such an animal that has been loved by humans as a pet from ancient times and, in modern times, called as Companion species, is becoming a member of a human society. On the other hand, a cat has hitherto greatly contributed to humans as an experimental animal in various fields such as medicine, pharmaceutics, animal husbandry veterinary and psychology, and in recent years, the contribution of a cat has further increased to be used in an effectiveness assay or safety test for drugs. With increasing social significance of a cat, there is a high interest in feline diseases, especially feline infectious diseases, and thus more efficacious method for treating these diseases is desired.

Many feline viral diseases, attack of which often leads to serious conditions, are known. For example, an upper tracheal disease caused by feline herpes virus type 1 (FHV-1) or feline calicivirus (FCV) is acute and highly lethal. In addition to this, diseases caused by feline immunodeficiency virus, feline infectious peritonitis virus, feline parvovirus, etc. are also highly lethal and have been great concern. Although some prophylactic vaccines have been developed for these viral diseases, many of these vaccines are not fully efficacious due to diversity of viral serotype. Furthermore, once a cat is infected with virus and after the onset of viral diseases, vaccines are not substantially efficacious any more, and hence, protection from secondary bacterial infections with antibiotics, sulfonamides etc. or symptomatic treatment with vitamins or nutrients have primarily been carried out. That is, presently no efficacious medicaments are available for treating the viral diseases.

Host immunity to microorganisms including viruses consists of a humoral immunity by an antibody and a cellular immunity by a lymphocyte. A cellular immunity reaches at its maximum level seven to ten days after infection and thereafter declines rapidly. On the other hand, antibody production starts to increase a week after infection, reaches at its maximum level around three to four weeks after infection and thereafter declines slowly. Since a neutralizing antibody is effective at the early stage of viral infection as well as passive immunity, the crux of developing a vaccine for prophylaxis of diseases is to produce a neutralizing antibody in any way. Once infection has been established, however, a neutralizing antibody does not usually function effectively with the lapse of time after infection. Moreover, a neutralizing antibody is not so effective in case of a persistent infection (e.g. herpes virus) wherein a virus remains within cells and infects through cells to cells or in case that a virus is likely to mutate even after infection to exhibit resistance against a neutralizing antibody (e.g. immunodeficiency virus). In such cases, it is generally believed that only a cellular immunity is effective which is mediated by cytotoxic T lymphocytes (CTL) which find out and eliminate those cells infected with virus. In general, a cytotoxic activity declines as symptoms became serious with the lapse of time after infection, resulting in more serious symptoms. In this context, if cytotoxic T lymphocytes could be activated, then the progress of disease can be retarded and rapid recovery will be expected (A. Capron et al., Current Topics in Microbiology and Immunology 189 Springer-Verlag, 1994).

There is a human therapy by activation of cytotoxic T lymphocytes wherein cytotoxic T lymphocytes are recovered from peripheral blood and, after nonspecific activation in vitro, reintroduced into the living body. In case of cats, however, this therapy is not applicable since sufficient amount of cytotoxic T lymphocytes cannot be recovered from peripheral blood due to a small body size of cats. That is, at present, there is not found any therapy for effective treatment of feline viral infectious diseases through activation of cytotoxic T lymphocytes. Although significance of a cellular immunity for treating viral infectious diseases is suggested, there has not hitherto been reported a cellular immunity-based medicament for feline viral infectious diseases, especially a medicament for activating cytotoxic T lymphocytes.

A cytokine is possibly involved in activation of cytotoxic T lymphocytes. Feline cytokines reported hitherto include, for example, erythropoietin (D. Wen et al., Blood Vol. 82, 1507–1516, 1993), a interferon (J. T. Yamamoto et al., Vet. Immunol. Immunopathol. Vol. 11, 1–19, 1986), and the like. However, there has hitherto been no report that any of these cytokines activated cytotoxic T lymphocytes. On the other hand, human or mouse interleukin 12 (hereinafter referred to as "IL12") is known which has an ability to activate T lymphocytes or to induce y interferon and activates cytotoxic T lymphocytes. Human and mouse IL12s cloned hitherto are known to exhibit the activity with a heterologous dimer consisting of an alpha chain (p35) and a beta chain (p40) (Annu. Rev. Immunol. Vol. 13, 251–276, 1995). It is also reported that human and mouse IL12 s show species specificity (S. F. Wolf et al., J. Immunol. Vol. 136, 3074–3081, 1991). As to feline IL12, a partial amino acid sequence of p35 has been reported (K. Bush et al., Molecular Immunology, Vol. 31, 1373–1374, 1994) with no disclosure of a biological activity of IL12 while an amino acid sequence of p40 has not yet been reported. Accordingly, at present, there is no substantial report as to feline cytokines which activate cytotoxic T lymphocytes.

DISCLOSURE OF THE INVENTION

Under the circumstances, the present inventors have thoroughly studied in order to find out feline cytokines which activate cytotoxic T lymphocytes, and as a result, have found a proteinaceous agent (novel feline cytokine) which enhances a cytotoxic activity of feline lymphocytes (especially cytotoxic T lymphocytes: CTL) in a culture supernatant of activated feline splenocytes. Furthermore, the present inventors have isolated and purified the novel feline cytokine protein from the recovered culture supernatant, elucidated their properties, expressed them in an animal cell with a gene engineering technique, and found that the resulting novel feline cytokine protein had an activity to enhance the cytotoxic activity of feline cytotoxic T lymphocytes, thereby completing the present invention.

That is, an object of the present invention is to provide a novel feline cytokine protein which enhances a cytotoxic activity of feline cytotoxic T lymphocytes as well as a polypeptide comprising a partial amino acid sequence of said novel feline cytokine protein.

Another object of the present invention is to provide a gene coding for a novel feline cytokine protein which enhances a cytotoxic activity of feline cytotoxic T lymphocytes or a polypeptide comprising a partial amino acid sequence of said novel feline cytokine protein as well as a recombinant DNA molecule for expressing said gene.

Further object of the present invention is to provide a process for preparing a novel feline cytokine protein which enhances a cytotoxic activity of feline cytotoxic T lymphocytes and a polypeptide comprising a partial amino acid sequence of said novel feline cytokine protein from microorganisms or animal cells transformed with said recombinant DNA molecule.

Still further object of the present invention is to provide a monoclonal antibody and a polyclonal antibody produced by using as an immunogen the thus obtained novel feline cytokine protein or the polypeptide comprising a partial amino acid sequence of said novel feline cytokine protein.

Still another object of the present invention is to provide an agent for treating feline viral infectious diseases comprising as an active ingredient the novel feline cytokine protein which enhances a cytotoxic activity of feline cytotoxic T lymphocytes.

The novel feline cytokine proteins as found out by the present inventors are a protein with a molecular weight of about 40,000 having the amino acid sequence as shown in Sequence Listing, SEQ ID NO: 1 or SEQ ID NO:2 (hereinafter also referred to as "FLAF p40"), and a protein with a molecular weight of about 35,000 having the amino acid sequence as shown in SEQ ID NO: 3 or SEQ ID NO: 4 (hereinafter also referred to as "FLAF p35"). The present invention also encompasses a peptide comprising a partial amino acid sequence of these proteins.

The present invention also encompasses a polyclonal antibody and a monoclonal antibody prepared by using as an immunogen the novel feline cytokine protein or the peptide having a partial amino acid sequence of said protein. Furthermore, the present invention encompasses an antibody obtained by introducing an expression vector wherein a gene coding for the polypeptide or a part of said gene is incorporated into an animal body in a conventional manner for expression within said animal body.

The present invention also encompasses gene fragments which code for the novel feline cytokine protein and have the nucleotide sequence as shown in SEQ ID NO: 5, 6 or 7 for FLAF p40 or the nucleotide sequence as shown in SEQ ID NO: 8 or 9 for FLAF p35, a gene fragment coding for a peptide comprising a partial amino acid sequence of said protein, as well as a recombinant DNA molecule comprising these gene fragments.

In addition, the present invention encompasses a transformant (*E. coli*, yeast, an insect cell, an animal cell, a plant cell) transformed with an expression vector such as a plasmid comprising the recombinant DNA molecule. The present invention also encompasses a process for preparing a desired novel feline cytokine protein or a peptide comprising a partial amino acid sequence of said protein by using said transformant.

BRIEF EXPLANATION OF THE DRAWINGS

FIG. 9 shows a nucleotide sequence overlapping between 2 clones (clones 12 and 25) obtained after screening of cDNA library as well as a corresponding amino acid sequence.

FIG. 13 shows a nucleotide sequence of FLAF p35 (clone 20) obtained by screening of cDNA library as well as a corresponding amino acid sequence, which depicts a region of the amino acid sequence that is distinct from the reported feline IL12 p35.

FIG. 16 is a photograph showing the results of testing for reactivity with serum from rabbit administered with CAGfp40 wherein purified FLAF is subjected to sodium dodecyl sulfate polyacrylamide gel electrophoresis (SDS-PAGE) in the absence of 2-mercaptoethanol and then transferred to a thin membrane where reactivity with the serum is investigated.

BEST MODE FOR PRACTICING THE INVENTION

Figure 1:
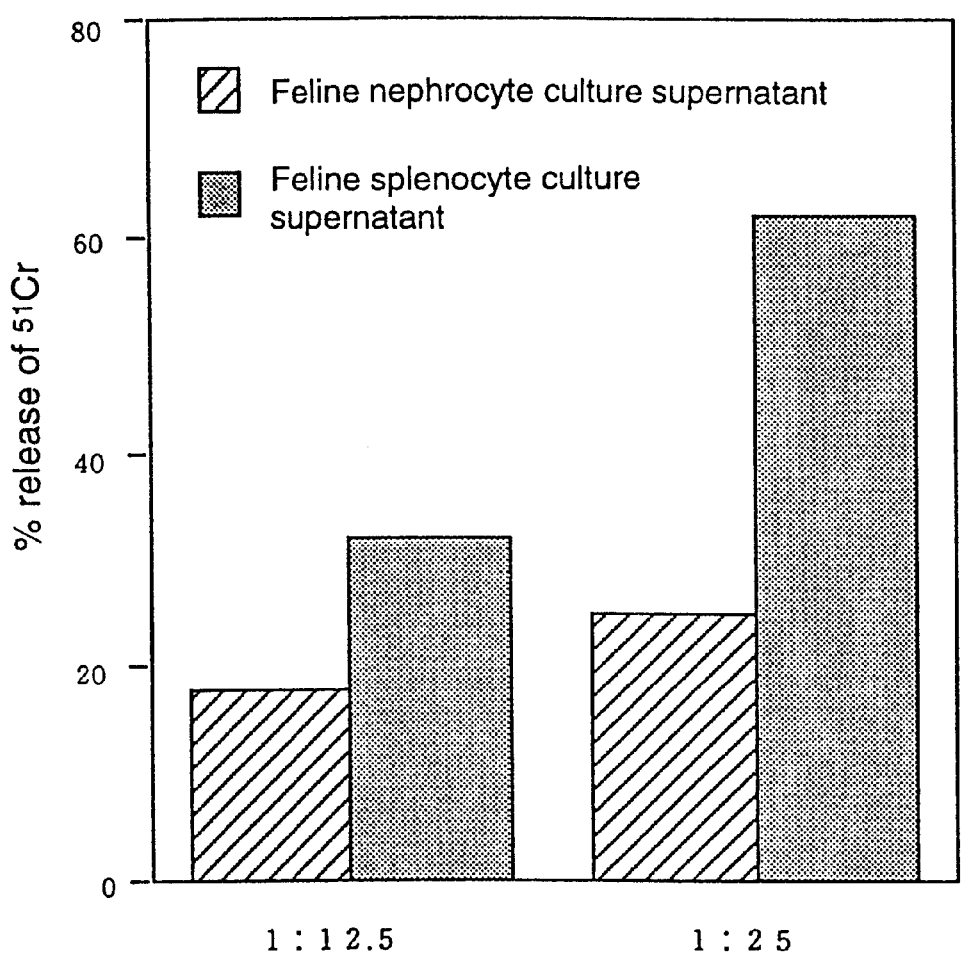
FIG. 1 shows the CTL enhancing activity observed in culture supernatant of feline splenocytes with culture supernatant of feline kidney cells being used as a negative control.

The present invention is explained in more detail hereinbelow.

The novel feline cytokine protein of the present invention can be purified by culturing feline lymphocytes in the presence of a lymphocyte mitogen and using as an index of purification the activity of cytotoxic T lymphocytes from the recovered culture supernatant.

For feline lymphocytes, splenocytes are preferably used but peripheral blood monocytes (PBMC) or some blood cancer cells may also be used. These cells may be cultured in a conventional procedure for cell culture, for example, as described in Culture of Animal Cells 2 nd Ed., Alan R. Liss, Inc., 1987. A lymphocyte mitogen includes phytohemagglutinin, concanavalin A, lipopolysaccharide, poke-weed mitogen with poke-weed mitogen (PWM) being preferred.

For measuring the activity of cytotoxic T lymphocytes as an index of purification, several methods are known and available. The most direct method is a $^{51}$Cr release assay wherein the activity of cytotoxic T lymphocytes to destroy $^{51}$Cr labelled target cells is measured. Indirectly, γ interferon released when cytotoxic T lymphocytes are activated can be measured. In these assay systems, it is desirable to use feline peripheral blood lymphocytes (PBL) as target cells. However, the use of feline PBL is not suitable for (1) CTL assay requiring persistently infected cells since most of the viruses known at present cause cytolysis after infection, and for (2) an assay system at each purification step which requires measurement of many samples since lymphocytes obtainable from an individual cat is not abundant in number while much more fresh peripheral blood monocytes (PBMC) are required for each assay.

Under the circumstances, the present inventors have found that the CTL assay ($^{51}$Cr release assay) system with human PBMC which has been established for influenza virus (Gorse et al., J. Clinical Microbiology, Vol. 28, 2539–2550 (1990)) can be utilized for measuring the activity of the feline cytokine protein to activate lymphocytes. A target virus to be used in this assay system is not limited to influenza virus but human herpes simplex virus (HSV) may also be used. However, usable virus is not limited to HSV but any virus which persistently infects during measurement of the CTL activity may be used.

The novel feline cytokine protein of the present invention may be isolated and purified using the ability to activate lymphocytes as an index by the usual methods employed in protein chemistry such as a salting out, an ultrafiltration, an isoelectric precipitation, an electrophoresis, an ion exchange chromatography, a hydrophobic chromatography, a gel filtration chromatography, a reverse phase chromatography, an affinity chromatography, and the like. Preferably, the novel feline cytokine protein is purified by successively conducting an anion exchange chromatography, a cation exchange chromatography, a heparin column chromatography, and a gel filtration chromatography under the conditions described in Example 2. According to these procedures, the novel feline cytokine protein can be purified up to 13% of an activity yield and a higher specific activity by 2350 folds with an index of the γ interferon inducing activity.

Figure 8:
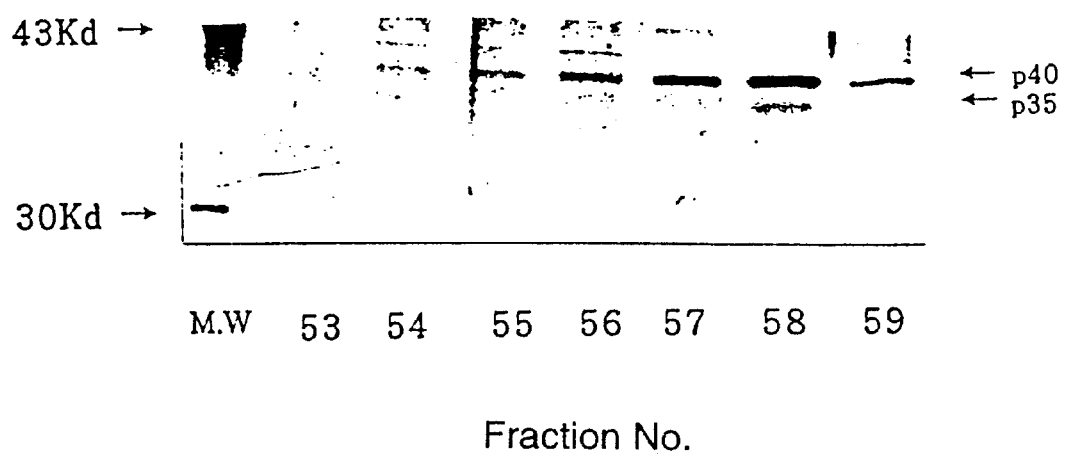
FIG. 8 is a photograph showing the results of sodium dodecyl sulfate polyacrylamide gel electrophoresis (SDS-PAGE) of the fractions with the γ interferon inducing activity obtained in FIG. 7 after treatment with 2-mercaptoethanol, which depicts both p40 and p35 associated with the activity.

The thus obtained purified fractions are then subjected to sodium dodecyl sulfate polyacrylamide gel electrophoresis (SDS-PAGE) in the presence of 2-mercaptoethanol to give unique bands associated with the γ interferon inducing activity, i.e. a main band of a molecular weight about 40,000 (FLAF p40) and a minor band of about 35,000 (FLAF p35) (cf. FIG. 8). An amino acid sequence of these unique bands can be determined by a usual method such as Edman degradation (P. Edman, Acta Chem. Scand., 4, 283 (1950)). As a result, FLAF p40 proved to be a novel feline protein. On the other hand, FLAF p35 was confirmed to be a peptide comprising the feline IL12 p35, to which C terminal is attached 19 amino acid residues:

Ala-Phe-Arg-Ile-Arg-Ala-Val-Thr-Ile-Asn-Arg-Met-Met-Ser-Tyr-Leu-Asn-Ser-Ser as shown in SEQ ID NO: 10 as compared with the amino acid sequence of feline IL12 p35 disclosed in Bush et al. supra. It was also found that the signal sequence included substitution of an amino acid at two sites ($^{-21}$Arg, $^{-20}$Gly; the numbering of an amino acid residue was in accord with SEQ ID NO: 3) and insertion of 3 amino acid residues:

Asn-His-Leu at the C terminal of $^{-10}$Leu (FIG. 13).

FLAF p40 and FLAF p35 genes may be cloned in a usual manner by preparing mRNA and cloning cDNA as taught by Maniatis et al. (Molecular cloning, A Laboratory Manual 2 nd Ed., 12.30, Cold Spring Harbor Laboratory Press, N.Y., 1989). Briefly, a whole RNA is prepared from feline lymphocytes cultured in the presence of a lymphocyte mitogen, a cDNA library is prepared therefrom, and FLAF p40 and FLAF p35 genes are screened from the library by using synthetic oligonucleotides prepared based on a partial amino acid sequence of FLAF p40 and FLAF p35 as a probe. A lymphocyte mitogen includes phytohemagglutinin, concanavalin A, lipopolysaccharide, poke-weed mitogen with poke-weed mitogen (PWM) being preferred. Feline lymphocytes include splenocytes, peripheral blood monocytes (PBMC), some blood cancer cells, and the like, with feline splenocytes being preferred. As a preferable probe, oligonucleotides designed on the basis of the N terminal 20 amino acid sequence of FLAF p40 and the N terminal 10 amino acid sequence of FLAF p35, respectively. Alternatively, each of FLAF p40 and FLAF p35 proteins is subjected to limited proteolysis, the resulting peptides are isolated by a reverse phase chromatography, and an N terminal amino acid sequence is determined and used for designing oligonucleotides. As to FLAF p35, since the N terminal sequence is identical to that of feline IL12 p35 (K. Bush et al., Molecular Immunology, Vol. 31, 1373–1374 (1994)), it is also possible to utilize the sequence to design an oligonucleotide or a PCR primer and the PCR products may be used.

A nucleotide sequence of the thus cloned FLAF p40 and FLAF p35 cDNAs may be determined with a DNA sequencer (Applied Biosystems, Model 1373A). Novelty of these cDNAs may be confirmed by investigating homology between the whole nucleotide sequence of these cDNAs and the known sequences in data base (for example, GeneBank, SWISS-PROT, etc.).

FLAF p40, FLAF p35, or a portion of each of these peptides, a heterologous dimer of FLAF p40 and FLAF p35 (hereinafter often referred to as "FLAF"), or a homologous dimer of FLAF p40 may be produced by preparing a recombinant DNA molecule wherein a full length of FLAF p40 cDNA, FLAF p35 cDNA, or cDNA fragment comprising a portion of the cDNAs is incorporated into a suitable expression vector, transforming a suitable microorganism or an animal cell with the recombinant DNA molecule, and culturing the resulting transformant. A peptide synthesizer may also be used for producing a portion of FLAF p40 or FLAF p35.

A suitable signal sequence for secretion in a microorganism or an animal cell may be linked upstream of the DNA coding for the protein of the present invention so that said protein is secreted into a culture medium. Such a modified DNA for secretion is advantageous in that the protein secreted into the culture medium can easily be recovered. A signal sequence includes pel B signal (S. P. Lei, et al., J. Bacteriology, Vol. 169, 4379–4383, 1987) for $E.\ coli$, $\alpha$ factor signal (A. J. Brake, Yeast Genetic Engineering, p269, Butterworth, 1989) for yeast, a signal of immunoglobulin, e.g. SG-1 antibody (H. Maeda et al., Hum. Antibod. Hybridomas, Vol. 2, 124–134, 1991) and C25 antibody (patent, International Publication No. WO94/20632) for an animal cell, and the like. However, not limited to these, any signal sequence may be employed insofar as it functions as a signal sequence.

Figure 10:
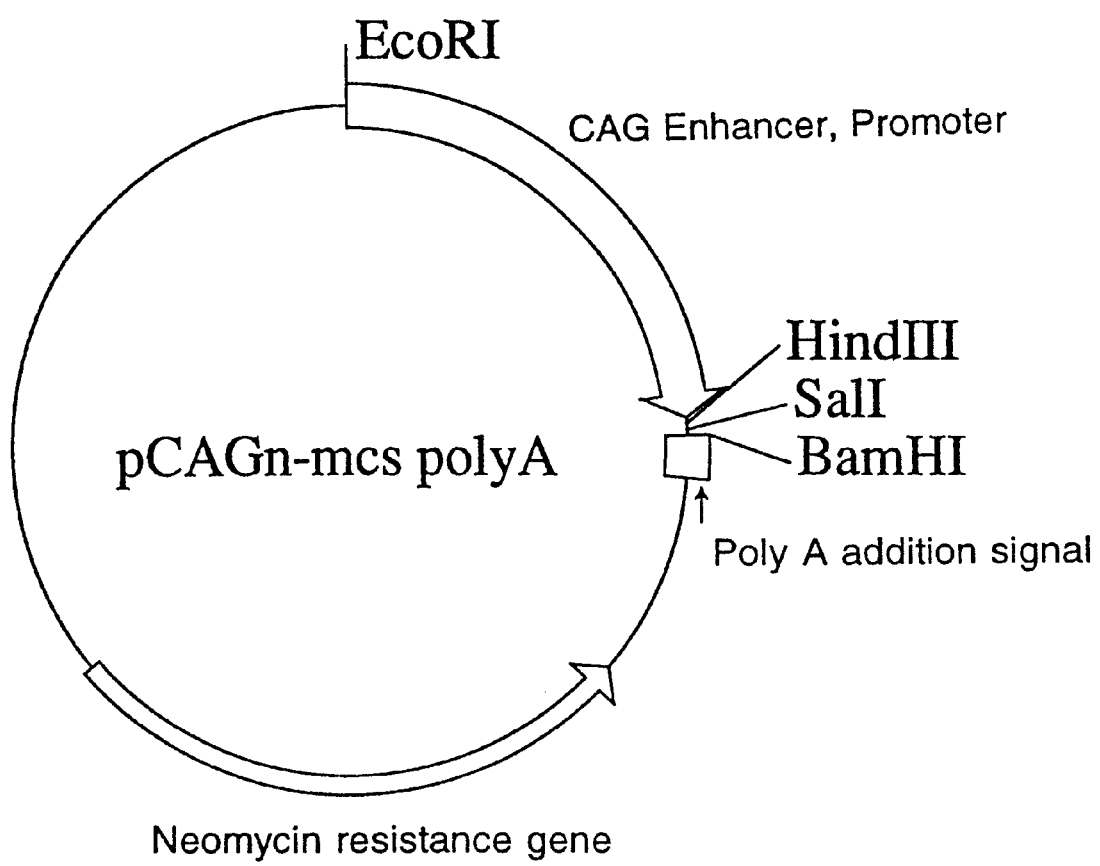
FIG. 10 illustrates an expression vector for animal cell, pCAGn-mcs polyA, which contains human cytomegalovirus enhancer, chicken β actin promoter and rabbit β globin splice acceptor as an expression control region.

An expression vector includes a plasmid, a viral vector, and the like. A promoter to be contained in the expression vector may be any promoter which is selected depending on a microorganism or an animal cell used as a host so that an active FLAF is ultimately obtained, including SV40 early promoter, SV40 late promoter, βactin promoter, etc. A marker gene may be used including an ampicillin resistance gene or a tetracycline resistance gene for $E.\ coli$ or Leu2 gene for yeast in case of an expression vector for a microorganism. In case of an expression vector for an animal cell, aminoglycoside 3'-phosphotranferase (neo) gene, dihydrofolate reductase (dhfr) gene, glutamine synthetase (GS) gene and the like may be used. FIG. 10 illustrates pCAGn-mcs polyA by way of example of such an expression vector. A typical substance added for selection includes G-418, methotrexate, methionine sulphoximine, and the like.

In case of an expression vector for an animal cell, a host cell includes various cells such as Chinese hamster ovary (CHO) cell, mouse myeloma cell, and COS cell. With a combination of the thus constructed FLAF p35 cDNA and FLAF p40 cDNA expression vectors, FLAF may transiently be expressed in, for example, COS7 cell (derived from African green monkey) or stably expressed in SFT34 cell (patent, International publication No. WO94/12658) or CHO cell as a host.

A host cell is transformed by a known method including, for example, a calcium phosphate method, a DEAE dextran method, a precipitation method using lipofectin etc., a method of fusing protoplasts with polyethylene glycol, a electroporation method, and the like. A suitable method for transformation may be selected depending on a host cell used.

The novel feline cytokine protein of the present invention is prepared in the manner described below. The cells stably expressing FLAF are cultured under conditions usually used for lymphocytes, for example, in RPMI medium containing 1 mg/ml G418 and 10% FCS in case that G418-resistant gene (Neo gene) is used as a selection marker, to give G418-resistant cells, and FLAF-producing transformants are screened by an assay using the γ interferon inducing activity as an index. If necessary, cloning is made by a limiting dilution technique to isolate said FLAF-producing clones. The thus obtained FLAF-producing transformants are cultured in a large scale, and FLAF is purified from the recovered culture supernatant in a similar manner to the above procedures by using as an index an immunochemical activity such as the activity of cytotoxic T lymphocytes or an antibody against FLAF so that the novel feline cytokine protein is produced.

The novel feline cytokine protein thus obtained has the enhanced activity to enhance the cytotoxic activity of feline cytotoxic T lymphocytes. The novel feline cytokine protein is used as an agent for treating feline viral infectious diseases or as an anti-cancer agent, which alone or in combination with a suitable pharmaceutically administrable carrier, diluent or stabling agent, is conventionally formulated into dosage forms such as injections, oral drugs, suppositories, or eye drops.

The novel feline cytokine protein of the present invention can be used for treatment of feline viral diseases including, for example, an upper tracheal disease caused by feline herpes virus type 1 (FHV-1) or feline calicivirus (FCV), viral infectious diseases with feline immunodeficiency virus, feline infectious peritonitis virus, feline parvovirus, feline panleukopenia virus, or feline leukemia virus. The novel feline cytokine protein of the present invention can also be used as an anti-tumor agent or a parasiticidal agent due to its activity to activate cytotoxic T lymphocytes.

The novel feline cytokine protein or a polypeptide comprising a partial amino acid sequence of said protein may be used as an immunogen for preparing a polyclonal antibody or a monoclonal antibody by the conventional method now established. An expression vector wherein a gene coding for the polypeptide or a portion of said gene is incorporated may be introduced into the animal body where said gene is expressed so that an antibody against said polypeptide or partial peptide of said polypeptide is produced. The thus produced antibody, which binds to the novel feline cytokine protein or a polypeptide comprising a partial amino acid sequence of said protein, or said protein or said polypeptide may be used in a system for detecting an antigen such as Western blot or ELISA, and thus constitutes a diagnostic agent. The antibody may be bound to a suitable carrier to provide an affinity chromatography which can be used to purify the antigenic protein.

The present invention provides a heterologous dimer protein comprising FLAF p35 and FLAF p40 which exhibits the γ interferon inducing activity and the CTL enhancing activity as well as cDNAs coding for each of these proteins.

FLAF p40, which the present inventors have firstly found, is a novel protein which hitherto never been reported and is one of important subunits constituting a molecule having the activity to activate feline lymphocytes to lead to destruction of viral infected cells. Furthermore, in accordance with the present invention, a whole amino acid sequence of the FLAF p35 molecule constituting the novel feline cytokine protein is determined to thereby reveal that the 19 amino acid residues attached at the C terminal of the reported amino acid sequence of the feline IL12 p35 is essential for the ability of activating lymphocytes. As mentioned hereinabove, the present invention dissolves the technical problems associated with the practical use of FLAF such as isolation of a gene coding for the active FLAF, construction of an expression vector, preparation of cells stably expressing FLAF, and purification of FLAF, and thus allows for production of PLAF as an agent for treating feline viral infectious diseases on an industrial scale.

Since FLAF of the present invention is a nonspecific factor which is not specific to any particular virus, it can be applied to any virus in addition to herpes virus. Candidates for such a target virus include, for example, feline calicivirus, feline panleukopenia virus, feline leukemia virus, feline immunodeficiency virus, and the like. FLAF of the present invention can widely be applied to any immune reaction mediated by histocompatibility class I antigen since it activates CTL. As such, FLAF of the present invention is expected to exhibit anti-tumor activity.

The present invention is explained in more detail by way of the following Examples but it should not be construed to be limited thereto. In the following Examples, the reagents manufactured by Wako Pure Chemical Industries, Ltd., Takara Shuzo K.K., Toyobo K.K., GIBCO BRL or New England BioLabs were used unless otherwise mentioned.

Example 1

Feline Lymphocyte Activating Factor
(1) Measurement of feline lymphocyte activating factor in culture supernatant of feline splenocytes A human CTL enhancing activity against HSV-infected human cells was measured in the manner described hereinbelow. For human PBMC, PBMC from subjects tested positive for anti-HSV antibody was used and selected from Buffy Coat available from the Japanese Red Cross Society, Blood Center. Target cells were prepared as described below.

Human PBMC at a concentration of 1×10 /ml are cultured in RPMI medium (Nissui Seiyaku K.K.) containing 10% fetal calf serum (FCS) under the conditions of 37° C. and 5% $CO_2$ for 3 days. On Day 3, to the culture is added 5 μg/ml of phytohemagglutinin and culture is continued for additional four days. On Day 7 after initiation of culture, the lymphocytes are harvested by centrifugation (1,500 rpm, 5 minutes) and suspended in HSV ($10^8$ $TCID_{50}$) solution. After incubation at 37° C. for 1 hour, to the suspension is added RPMI and the mixture is centrifuged to remove HSV. This procedure is repeated twice and human PBMC is finally labelled with sodium $^{51}Cr$ (Amersham, CJS-11) in accordance with Gorse et al. (J. Clinical Microbiology Vol. 28, 2539–2550 (1990)) to give target cells.

Effector cells were prepared as described below. Anti-HSV antibody positive PBMC was suspended in part ($1 \times 10^7$) in HSV solution and incubated at 37° C. for 1 hour. To the suspension was added RPMI and the mixture was centrifuged. This procedure was repeated twice to remove HSV. To the resulting lymphocytes were added untreated lymphocytes $9 \times 10^7$ suspended in RPMI medium containing 10% FCS. Thereto was added 1/100 volume of concentrated culture supernatant of feline spleno-cytes or culture supernatant of feline kidney cells as a negative control. The lymphocytes were cultured under the conditions of 37° C. and 5% $CO_2$ for 7 days. On Day 7, the culture was Ficoll-centrifuged with Ficoll-Paque Plus (Pharmacia) at 1,500 rpm for 30 minutes to isolate the living cells which were used as effector cells.

CTL assay was initiated by mixing the target cells with the effector cells. The target cells and the effector cells (1:50, 1:25; total 200 μl) were mixed on 96 well microtiter plate (Coning) and incubated under the conditions of 37° C. and 5% $CO_2$ for 6 hours. Six hours later, $^{51}Cr$ in the culture medium of each well was measured with γ counter (Aroca, ARC-360) on harvesting kit (Dainippon Seiyaku K.K.). A release percent of specific $^{51}Cr$ was calculated as follows:

$$(n-min)/(Max-min) \times 100$$

wherein "n" means $^{51}Cr$ count released in each sample, "min" means $^{51}Cr$ count released in those wells where target cells alone were added without effector cells, and "Max" means $^{51}Cr$ count released in those wells where 10 μl of 10% Triton X-100 without effector cells so that $^{51}Cr$ is completely released. As is clear from the results obtained in this CTL assay, the culture supernatant of feline splenocytes significantly enhanced the CTL activity as compared with the negative control, feline kidney cells culture supernatant (FIG. 1). This assay revealed the CTL enhancing activity with high reproducibility. The obtained results proved that the concentrated culture supernatant of feline splenocytes exhibits the CTL enhancing activity to human PBMC, suggesting the presence of a lymphocyte activating factor in the concentrated culture supernatant of feline splenocytes.

(2) measurement of activity to induce γ interferon to human PBMC in culture supernatant of feline splenocytes As an index of lymphocyte activation, the γ interferon inducing activity is also known in addition to the CTL activation. Thus, the activity to induce γ interferon to human PBMC was measured in culture supernatant of feline splenocytes. The activity was measured as described below.

Figure 2:
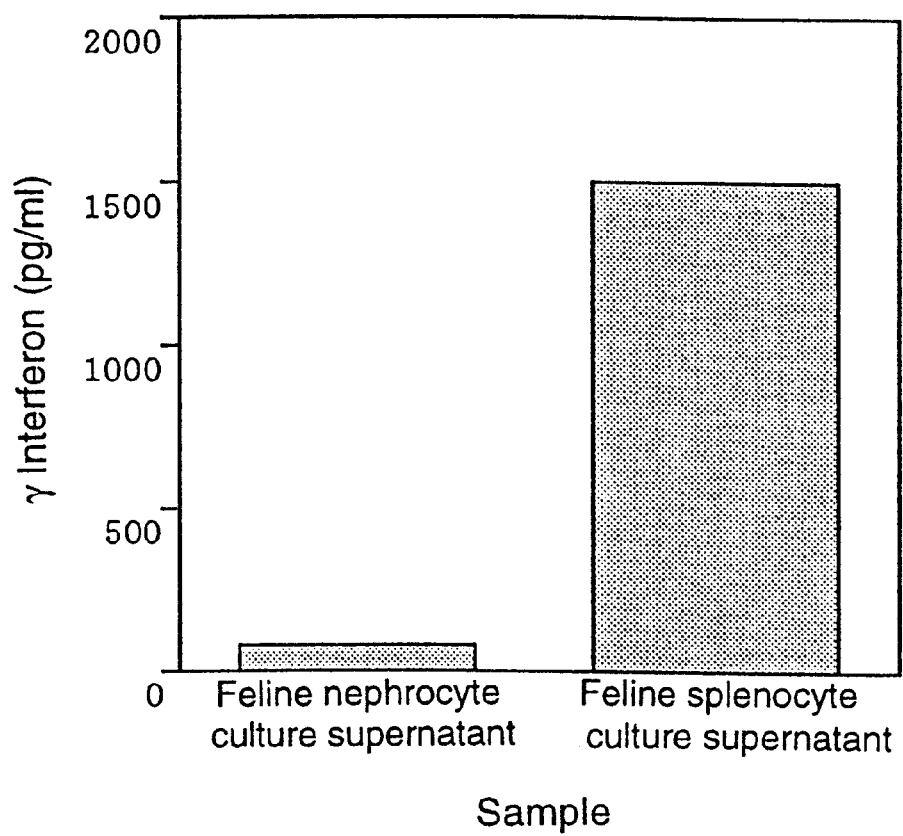
FIG. 2 shows the γ interferon inducing activity observed in culture supernatant of feline splenocytes with culture supernatant of feline kidney cells being used as a negative control.

Normal adults were bled with heparin and blood was Ficoll-centrifuged (1,500 rpm, 30 minutes) to prepared PBMC, which was filled in a 96 well plate at 1×10 /well. To the plate was added 1/10 volume of culture supernatant of feline splenocytes and incubated under the conditions of 37° C. and 5% $CO_2$ for 16 hours. As a negative control, culture supernatant of CRFK cells, known feline kidney cell line, was used. Sixteen hours later, the culture supernatant was harvested and human γ interferon in the culture supernatant was measured with EIA kit (Ohtsuka Kagaku Seiyaku K.K.). As a result, it was found that γ interferon was detected only in the wells where culture supernatant of splenocytes was added to prove that the culture supernatant of feline splenocytes has the activity to induce γ interferon to human PBMC (FIG. 2).

(3) Partial purification of a lymphocyte activating factor in culture supernatant of feline splenocytes In order to determine whether these two activities were attributable to a single factor, the concentrated culture supernatant of feline splenocytes was fractionated with an anion exchange chromatography to determine whether fractions having each of these activities were overlapped.

Culture supernatant (concentrated by 50 folds; 5 ml) of feline splenocytes was dialyzed against 20 mM Tris-HCl buffer (pH 8.0) containing 50 mM NaCl and then applied to Mono-Q (Pharmacia, HR5/5) column equilibrated with the same buffer at a flow rate of 0.5 ml/min. The column was washed with 5 ml of the above buffer and eluted by a salt gradient with 10 ml of 50 mM–500 mM NaCl/20 mM Tris-HCl (pH 8.0) at a flow rate of 0.5 ml/min to give each 1 ml of fractions. Each of fractions was dialyzed against PBS and then filtered with 0.22 μm filter.

Figure 3:
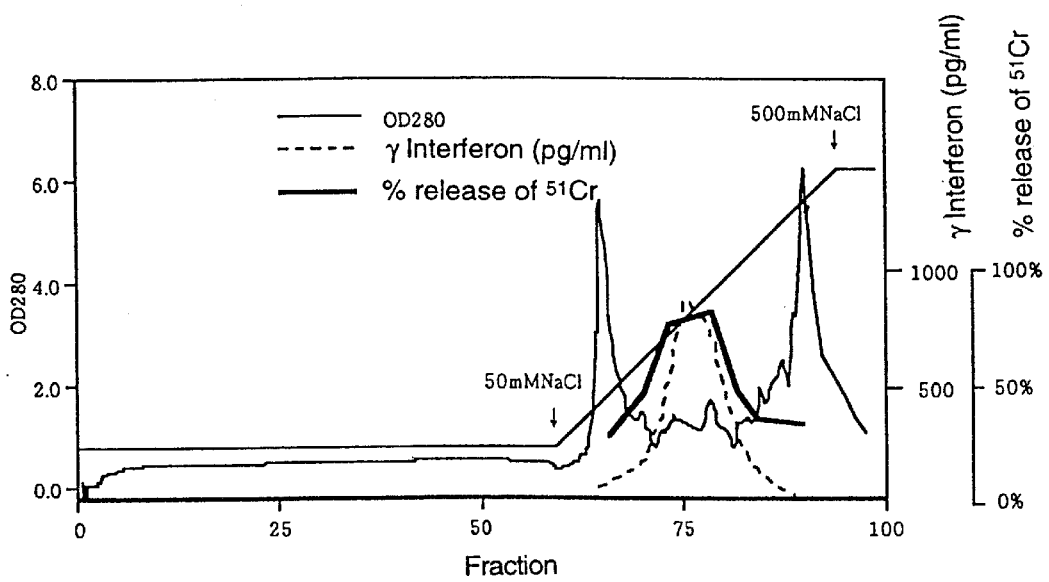
FIG. 3 illustrates a pattern obtained by fractionation of concentrated culture supernatant of feline splenocytes by an anion exchange chromatography (MonoQ), which depicts that both elution patterns of the γ interferon inducing activity and the $^{51}$Cr releasing activity are overlapping.

The CTL enhancing activity was measured for each of fractions by the above system using human PBMC and HSV (target cells: effector cells=1:25). As a result, it was shown that the CTL enhancing activity was exhibited by those fractions eluted at around 200 mM NaCl. The activity to induce γ interferon to human PBMC was also measured for each of fractions. As a result, it was found that the γ interferon inducing activity was also exhibited by those fractions eluted at around 200 mM NaCl like in the CTL enhancing activity. As shown in FIG. 3, a pattern of eluted fractions was well matched for the CTL enhancing activity and the γ interferon inducing activity, and thus both activities were attributable to a single molecule. This feline factor having these activities was referred to as a feline lymphocyte activating factor and was further purified. In the purification procedures described below, the γ interferon inducing activity was measured as an index activity.

Example 2

Figure 4:
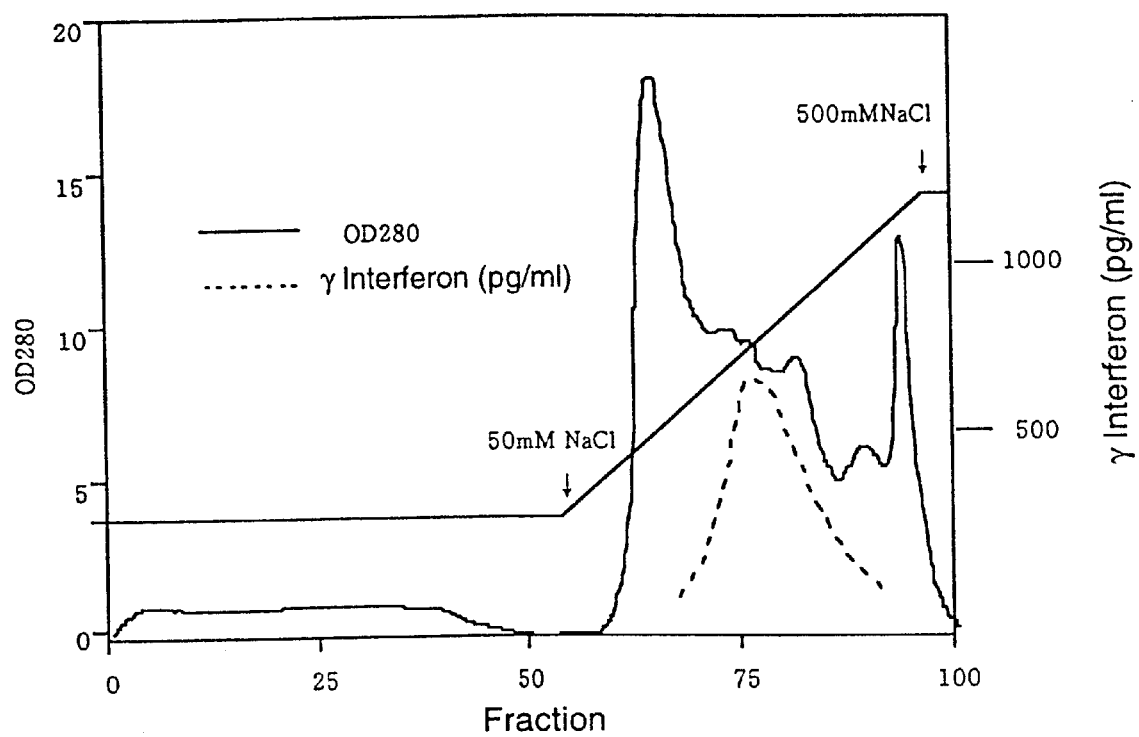
FIG. 4 illustrates a pattern obtained by fractionation of concentrated culture supernatant of feline splenocytes by an anion exchange chromatography (MonoQ), which depicts that those fractions with the γ interferon inducing activity are eluted with NaCl at a concentration ranging from 200 mM to 300 mM.

Purification of Feline Lymphocyte Activating Factor (1) Anion exchange chromatography Culture supernatant (concentrated by 50 folds; 200 ml) of feline splenocytes was dialyzed against 20 mM Tris-HCl buffer (pH 8.0) containing 50 mM NaCl and then applied at a flow rate of 2 ml/min to Mono-Q (Pharmacia, HR10/10) column equilibrated with the same buffer. The column was washed with 50 ml of the above buffer and eluted at a flow rate of 2 ml/min by a salt gradient with 200 ml of 50 mM–500 mM NaCl/20 mM Tris-HCl (pH 8.0). A portion of fractions was used to measure the γ interferon inducing activity. FIG. 4 shows the elution profile. The fractions having the activity were pooled and were dialyzed against 20 mM citrate buffer (pH 6.0) containing 100 mM NaCl.

(2) Cation exchange chromatography

Figure 5:
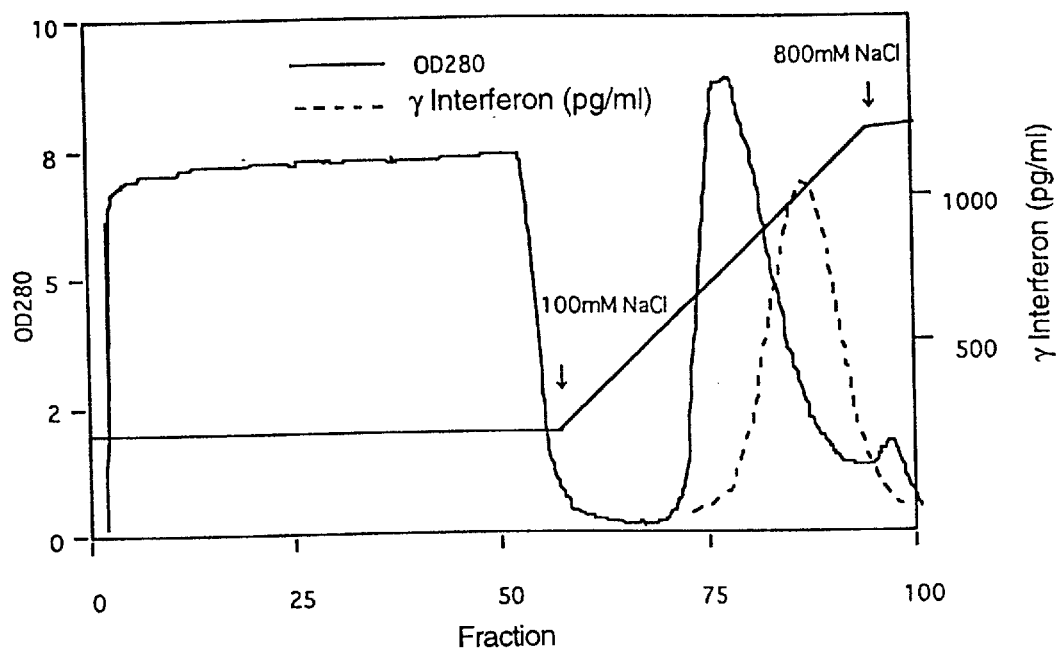
FIG. 5 illustrates a pattern obtained by fractionation of the fractions obtained in FIG. 4 by a cation exchange chromatography (SP Toyopearl), which depicts that those fractions with the γ interferon inducing activity are eluted with NaCl at a concentration ranging from 500 mM to 600 mM.

The dialysate obtained by the anion exchange chromatography was applied at a flow rate of 1 ml/min to SP-Toyopearl (Toso) column (1×8 cm) equilibrated with 20 mM citrate buffer (pH 6.0) containing 100 mM NaCl. The column was washed with 50 ml of the above buffer and eluted by a salt gradient with 100 ml of 100 mM–800 mM NaCl/20 mM citrate (pH 6.0) at a flow rate of 1 ml/min. A portion of fractions was used to measure the γ interferon inducing activity. FIG. 5 shows the elution profile. The fractions having the activity were pooled and were dialyzed against 10 mM phosphate buffer (pH 7.0) containing 200 mM NaCl.

(3) Heparin column

Figure 6:
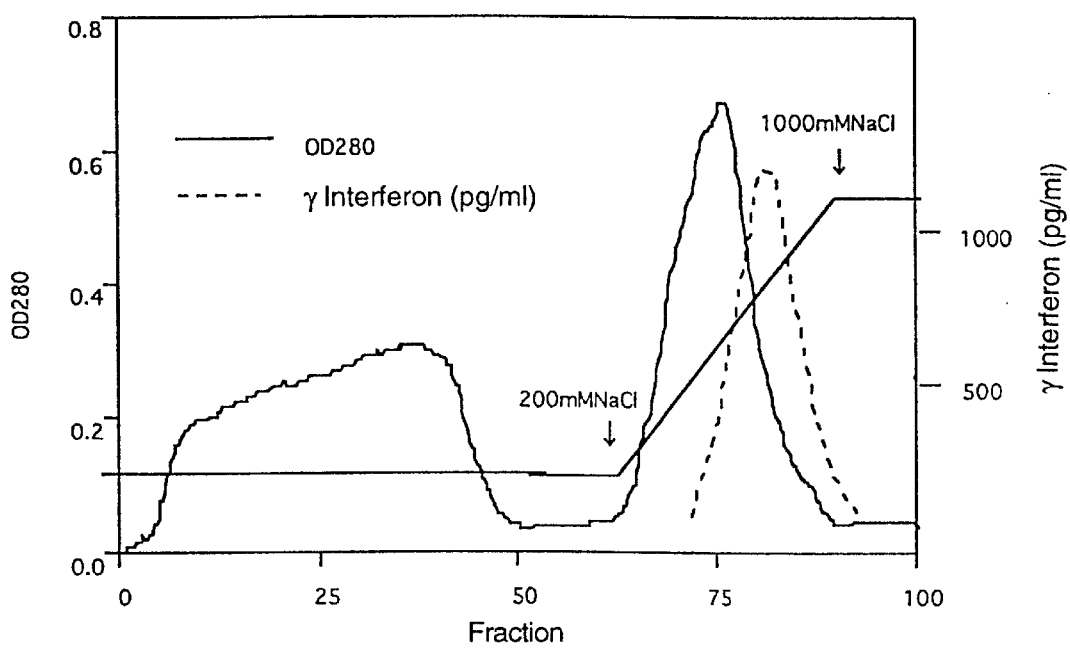
FIG. 6 illustrates a pattern obtained by fractionation of the fractions obtained in FIG. 5 by a heparin column chromatography (HiTrap Heparin), which depicts that those fractions with the γ interferon inducing activity are eluted with NaCl at a concentration ranging from 600 mM to 800 mM.

The dialysate obtained by the cation exchange chromatography was applied at a flow rate of 0.5 ml/min to HiTrap-Heparin (Pharmacia) which was washed with 20 ml of 10 mM phosphate buffer (pH 7.0) containing 200 mM NaCl and eluted by a salt gradient with 200 mM–1000 mM NaCl/10 mM phosphate buffer (pH 7.0). A portion of fractions was used to measure the γ interferon inducing activity. FIG. 6 shows the elution profile. Finally, 5 ml fractions having the activity were obtained and concentrated to 2 ml with Centricon-10 (Grace Japan).

(4) Gel filtration

Figure 7A:
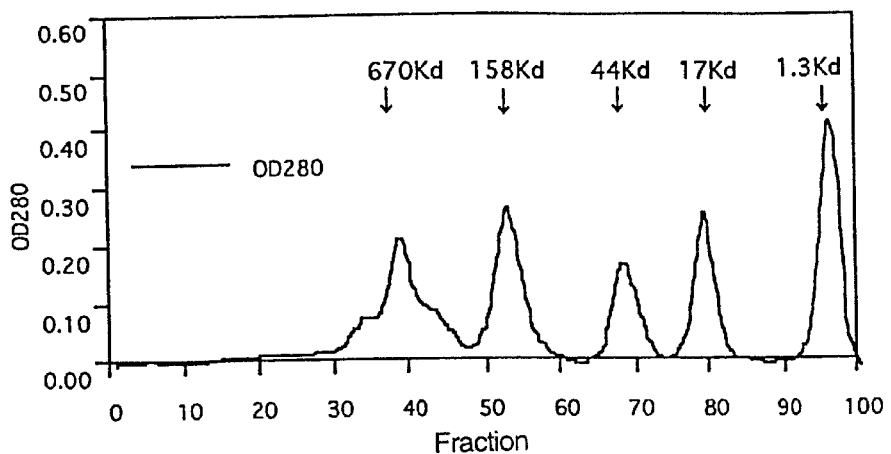
FIG. 7 illustrates a pattern obtained by fractionation of the fractions obtained in FIG. 6 by a gel filtration chromatography (HiLoad), which depicts that those fractions with the γ interferon inducing activity are eluted as fractions having a molecular weight ranging from 60,000 to 80,000.
Figure 7B:
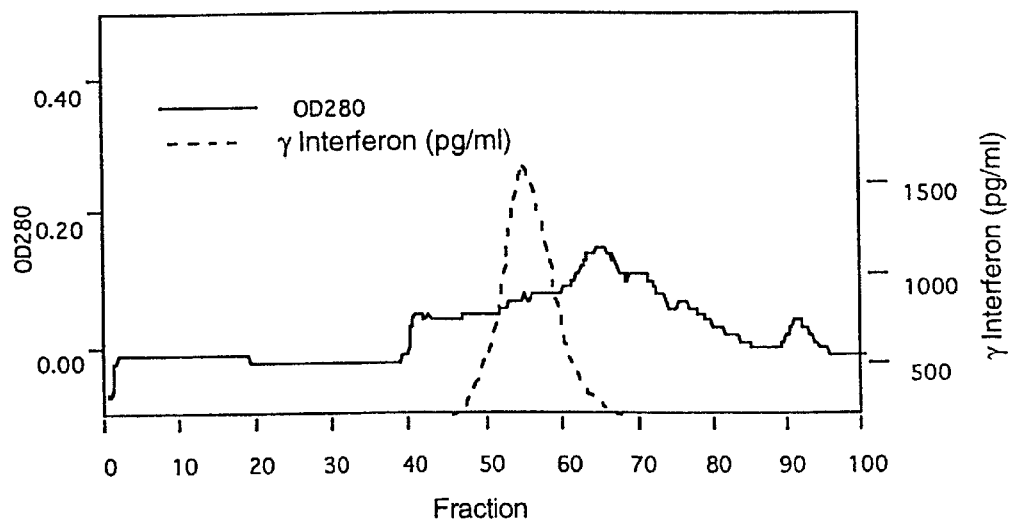

The concentrate obtained by the heparin column was applied to Gel filtration column HiLoad 16/60 (Pharmacia) equilibrated with 10 mM phosphate buffer (pH 7.0) containing 100 mM NaCl and fractionated at a flow rate of 0.5 ml/min. Markers of Gel filtration, Bio Rad, were used as a molecular weight standard. The γ interferon inducing activity was measured for each fraction to reveal a peak activity at fractions of molecular weight around 60,000 to 80,000 (FIG. 7).

As shown in Table 1, the feline lymphocyte activating factor could be purified up to 13% of an activity yield and a higher specific activity by 2350 folds with an index of the γ interferon inducing activity in accordance with the above 4 step purification procedures.

|  | Activity Induced (γ-IFN) | OD280 | Amount | Total activity | Yield | Specific activity Induced γ-IFN / OD280 | Purification degree |
|---|---|---|---|---|---|---|---|
| Feline splenocyte culture | 0.2 ng/ml | 0.12 | 6000 ml | 1200 | 100% | 1.7 | 1 |
| Mono Q | 9 | 0.63 | 50 | 450 | 38 | 14.3 | 8.4 |
| SP-Toyopearl | 58 | 0.05 | 5 | 290 | 24 | 1160 | 680 |
| Hi Trap Heparin | 75 | 0.03 | 3 | 225 | 19 | 2500 | 1470 |
| Hi Load | 80 | 0.02 | 2 | 160 | 13 | 4000 | 2350 |

Example 3

N Terminal Amino Acid Analysis of Feline Lymphocyte Activating Factor

Among the fractions fractionated by the gel filtration, those fractions exhibiting the γ interferon inducing activity were subjected to sodium dodecyl sulfate electrophoresis (SDS-PAGE) in the presence of 2-mercaptoethanol to prove a unique main band of a molecular weight of about 40,000 associated with the γ interferon inducing activity (FIG. 8). A minor band of a molecular weight of about 35,000 was also confirmed. Firstly, the protein having a molecular weight of about 40,000 was referred to as "PLAF p40" and an amino acid sequence of its N terminal was determined as described below.

The fractions with the activity were concentrated and, after treatment with 2-mercaptoethanol, subjected to SDS-PAGE with 10% polyacrylamide gel. After completion of electrophoresis, the gel was immersed into a transfer buffer (10 mM N-cyclohexyl-3-aminopropansulfonic acid, 10% methanol, pH 11) for 5 minutes, overlaid to PVDF membrane (Immovilon: Millipore), which has previously been immersed successively into 100% methanol and the transfer buffer, and the protein was transferred with TRANS- BLOTCELL (Bio Rad) at 160 mA for 16 hours. The PVDF membrane after transfer was washed with water, stained with 0.1% amide black (40% methanol, 1% acetic acid) for 1 minute and washed with distilled water.

The stained band of a molecular weight of 40,000 was excised and the membrane segment was analyzed with 477A Protein Sequencer (Applied Bio Systems). The N terminal amino acid sequence of 20 amino acid residues was determined as follows:

Ile-Trp-Glu-Leu-Glu-Lys-Asn-Val-Tyr-Val-Val-Glu-Leu-Asp-Trp-His-Pro-Asp-Ala-Pro as shown in SEQ ID NO:11. Homology search was carried out for this sequence with GENETYX software to prove that this protein had homology with human and mouse IL12 p40. However, the protein of this sequence has never been reported in cats.

Example 4

Cloning of FLAF p40 Gene

In order to confirm that FLAF p40 actually possesses the CTL enhancing activity or the γ interferon inducing activity, an FLAF p40 gene was firstly isolated from activated feline splenocyte cDNA library. The cDNA library was prepared as described below.

First, a whole RNA was prepared from feline splenocytes (cultured in the presence of 0.01% PWM for 18 hours, $3 \times 10^8$) with ISOGEN reagent (Nippon Gene) and its protocol. Poly A+RNA was prepared from the whole RNA with poly(A) quick mRNA isolation kit (STRATAGENE). Feline splenocyte cDNA library was prepared from the poly A+RNA with Uni-ZAP XR vector kit (STRATAGENE) and its protocol. As a probe for screening, the sequence:

Ile-Trp-Glu-Leu-Glu-Lys-Asn-Val-Tyr-Val-Val-Glu-Leu was selected from the N terminal amino acid sequence of 20 amino acid residues of SEQ ID NO: 11 which was determined by analysis df the N terminal amino acid sequence of FLAF p40, and an oligonucleotide:

ATCTGGGA(G,A)CT(G,C)GA(G,A)AA(G,A)AACGT(G,C)TACGT(G,C)GT(G,C) GA(G,A)CT as shown in SEQ ID NO: 12 was designed and synthesized by employing those codons used in cats at high frequency. Using this probe, screening was carried out for $3 \times 10^6$ plaques as described in Molecular cloning, A Laboratory Manual 2 nd Ed., 12.30, Cold Spring Harbor Laboratory Press, N.Y., 1989 to give 2 positive plaques.

A nucleotide sequence of these cDNAs was determined to prove that clone No. 12 had a nucleotide sequence coding for the amino acid sequence which is completely identical to the N terminal sequence of FLAF p40. When the same frame as the N terminal sequence of FLAF p40 was aligned to the nucleotide sequence of clone No. 12, it was revealed that an open reading frame had an insert DNA of 500 bp in length and no termination codon. Thus, it was estimated that this cDNA does not encode a full length of FLAF p40. *E. coli* 92314 wherein plasmid (pFLAF12) comprising this clone No. 12 is incorporated has been deposited by the applicant in accordance with the Budapest Treaty under accession number FERM BP-5877 at National Institute of Bioscience and Human-Technology Agency of Industrial Science and Technology, 1–3, Higashi 1-chome, Tsukuba-shi, Ibaraki-ken, 305, Japan, on Mar. 14, 1997.

In order to obtain a clone of cDNA comprising a full length of FLAF p40, feline splenocyte cDNA library was screened with a probe prepared on the basis of the insert region of the clone No. 12. Plaques ($1 \times 10^6$) were screened to give 1 positive clone (clone No. 25). A nucleotide sequence of the insert region of this clone No. 25 was determined to prove that about 30 bp at the 5' terminal of this clone was overlapped with about 30 bp of the 3' terminal of the clone No. 12 and the 3' terminal of the clone No. 25 comprises termination codon and poly A. *E. coli* 92315 wherein plasmid (pFLAF25) comprising this clone No. 25 is incorporated has been deposited by the applicant in accordance with the Budapest Treaty under accession number FERM BP-5878 at National Institute of Bioscience and Human-Technology Agency of Industrial Science and Technology, 1–3, Higashi 1-chome, Tsukuba-shi, Ibaraki-ken, 305, Japan, on Mar. 14, 1997. A combined nucleotide sequence of the clones No. 12 and No. 25 is shown as SEQ ID NO: 5. This nucleotide sequence revealed that FLAF p40 protein comprises a signal peptide, consisting of 22 amino acids, and 307 amino acid residues. Homology search for this sequence showed that this protein is a novel feline protein.

Example 5

Expression of FLAF p40 Gene

For expression of cDNA coding for FLAF p40 in an animal cell, it was necessary to link the two clones obtained above together. However, since the overlapped region of these clones was quite short, i.e. only about 30 bp, linkage of these clones by cleavage with a suitable restriction enzyme and subsequent linkage was considered to be difficult. Thus, by changing the codon GTG for No. 160 Val (the numbering of an amino acid residue was in accord with SEQ ID NO:1) contained in both clones into GTC (Val) thereby to introduce SalI site into this portion, the two clones were linked together in the manner described below.

In order to introduce SalI site into the 3' terminal of the clone No. 12 and the 5' terminal of the clone No. 25, polymerase chain reaction (PCR) was carried out with each clone being a template. PCR reaction was carried out with Amplitaq DNA polymerase (Takara Shuzo) for 35 cycles, each cycle consisting of 95° C. for 1 minute, 60° C. for 2 minutes and 72° C. for 2 minutes, with T3 primer of pbluescript II SK+vector and a primer of the sequence:

GGGGTACCGTCGACTCTGACCTTCTCTGCTGA as shown in SEQ ID NO: 13 for the clone No. 12 and with T7 primer of pBluescript II SK+vector and a primer of the sequence:

GCTCTAGAAAGCTTGAATTCGTCGACAA-CAGGGATTATAAGAAG as shown in SEQ ID NO: 14 for the clone No. 25.

The PCR products of each of clones 12 and 25 were digested with BglII-KpnI and XbaI-XcmI enzymes, respectively, and the resulting DNA segments were ligated to pBluescript II SK+plasmids where each clone digested with the same set of restriction enzymes was purified, to introduce SalI site into each of the clone Nos. 12 and 25 on the pBluescript II SK+plasmid.

The substituted regions were sequenced with Dye Primer Cycle Sequencing Kit and Model 1373A DNA sequencer (Applied Bio Systems) to confirm no error in the PCR reaction. Then, the clone 12 having SalI site was digested with EcoRI-SalI to prepare a 5' terminal DNA segment of FLAF p40, which was then incorporated into the EcoRI-SalI site of the clone No. 25 plasmid having SalI site to link these two DNA segments together to construct a full length p40 cDNA.

The thus obtained full length cDNA of FLAF p40 was incorporated into a suitable expression vector for an animal cell and an expression was carried out. pCAGn-mcs polyA (FIG. 10) was used as an expression vector. pCAGn-mcs polyA vector contains human cytomegalovirus enhancer and chicken β actin promoter as an expression control region and rabbit β globin splicing signal. After a SalI-EcoRI fragment of CAG enhancer promoter (H. Niwa et al., Gene, 108, 193 (1991)) was blunt-ended and inserted into the EcoRV site of pBluescript II SK+vector, the terminals were converted to EcoRI-HindIII site and then inserted into the EcoRI-HindIII site of pUC18 vector. An EcoRI-BamHI fragment was prepared from this plasmid and inserted into the EcoRI-BamHI site of pSV2neo vector where HindIII site is deprived (P. J. Southern et al., J. Mol. Appl. Genet., 1, 327 (1982)), to which BamHI site was further inserted a DNA fragment containing a polyA addition signal of BamHI-BglII derived from pCB25 γSD/BcBg plasmid (Japanese patent publication No. 3–201986) to construct pCAGn-mcs polyA vector.

The plasmid containing the full length cDNA of FLAF p40 was digested with a restriction enzyme HindIII-XhoI to cleave the FLAF p40 cDNA, which was inserted into the HindIII-SalI site of pCAGn-mcs polyA to construct a FLAF p40 expression vector. The obtained FLAF p40 expression plasmid (CAGfp40) was introduced into COS7 cells with Lipofect Ace reagent for transient expression.

Figure 11:
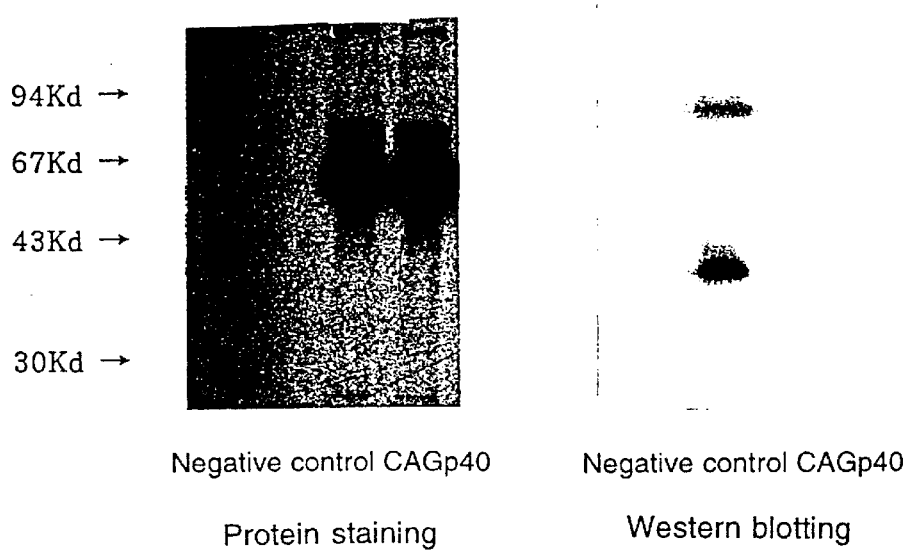
FIG. 11 is a photograph which proves the presence of a desired expression product when culture supernatant of transformed COS cells is treated with 2-mercaptoethanol, subjected to sodium dodecyl sulfate polyacrylamide gel electrophoresis (SDS-PAGE) and transferred to a thin membrane wherein culture supernatant of COS cells transfected with pCAGn-mcs polyA is used as a negative control.
Figure 12:
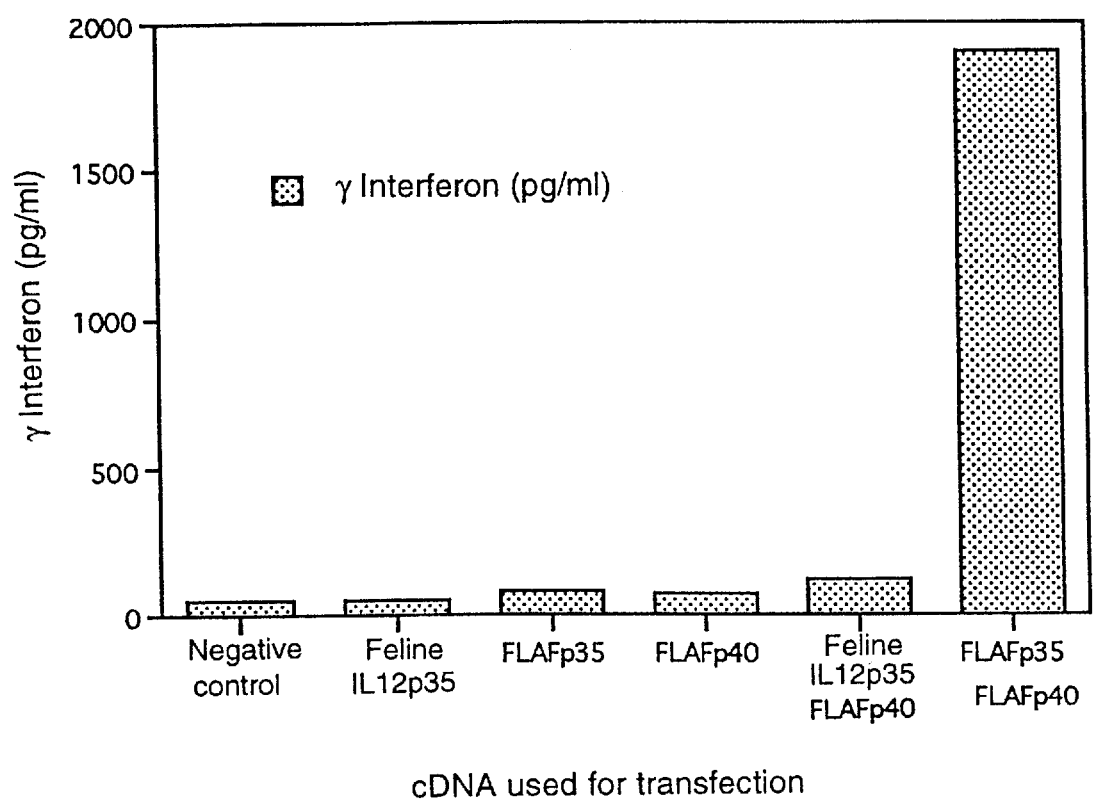
FIG. 12 shows the γ interferon inducing activity observed in culture supernatant of COS cells incorporated with expression vectors of FLAF p40, feline IL12 p35 or FLAF p35, each alone or in combination thereof, wherein culture supernatant of COS cells incorporated with an expression vector comprising no exogenous gene is used as a negative control.

The day (20 hours) before transfection, COS7 cells were plated on a 6 well plate at $2 \times 10^5$ cells/well. On the next day, Lipofect Ace reagent was mixed with the expression plasmid (1 μg of cAGf40 per well) and the mixture was left to stand at room temperature for 15 minutes and then added to the COS7 cells, followed by addition of serum free medium Opti-MEM (0.8 ml). On the next day, 2 ml of serum free medium (ASF104; Ajinomoto K. K.) was added and culture was continued for additional 2 days and then culture supernatant was recovered. A portion of the supernatant was subjected to Western blot as described in Example 11 to detect expression products which reacted with polyclonal antibodies which recognize FLAF p40. As a result, bands corresponding to FLAF p40 reactive with anti-FLAF p40 antibody (MW about 40,000) and to a homologous dimer thereof (MW about 80,000) were detected (FIG. 11). However, the culture supernatant exhibited no activity to induce γ interferon against human PBMC like the culture supernatant in the well where pCAGn-mcs polyA was used for transfection as a negative control (FIG. 12). That is, it was revealed that the γ interferon inducing activity exhibited by the fractions of molecular weight of around 60,000 to 80,000 during purification by gel filtration of the feline lymphocyte activating factor was not attributable to the homologous dimer of FLAF p40.

However, the homologous dimer of FLAF p40 of the present invention is expected to be an antagonist to the feline cytokine protein to show a feline cytokine protein. inhibiting activity like the homologous dimer of mouse IL12 β chain (p40) as reported by Germann et al., Immunology Today Vol. 16, p500–501 (1995).

Example 6

Cloning of Feline IL12 p35 Gene

FLAF p40 isolated herein alone did not show the γ interferon inducing activity. Since the γ interferon inducing activity exhibited during purification by gel filtration of the feline lymphocyte activating factor was not attributable to the homologous dimer of FLAF p40, it is possibly suggested that the activity is attributable to a complex formed between the FLAF p40 molecule and a distinct molecule having a similar molecular weight to that of FLAF p40. In view of its γ interferon inducing activity and molecular weight, the feline lymphocyte activating factor of the present invention may be homologous to human or mouse IL12 (heterologous dimer of p40 beta chain and p35 alpha chain). In this context, it is possible that the feline IL12 p35 with a molecular weight 35,000 as reported by Bush et al. is a partner of the FLAF p40 molecule of the present invention. Thus, a feline IL12 p35 gene coding for an amino acid sequence of feline IL12 p35 was cloned and relation between feline IL12 p35 and FLAF p40 was investigated.

Based on the N terminal and C terminal amino acid sequences of the feline IL12 p35 as reported by Bush et al., there were prepared a synthetic DNA (1) of the nucleotide sequence:

ATGTGCCC(A,G,C,T)CC(A,G,C,T)CT(A,G,C,T)TG(T, C)CT(A,G,C,T)

as shown in SEQ ID NO: 15 and a synthetic DNA (2) of the nucleotide sequence:

ATGTGCCC(A,G,C,T)CC(A,G,C,T)TT(A,G)TG(T,C) TT(A,G)

as shown in SEQ ID NO: 16 as a PCR primer corresponding to the N terminal sequence:

Met-Cys-Pro-Pro-Leu-Cys-Leu and, a synthetic DNA (3) of the nucleotide sequence:

(G,A)TG(A,G,C,T)AG(A,G,C,T)AG(A,G,T)ATGCA(A, G,C,T)AGCTT as shown in SEQ ID NO: 17 and a synthetic DNA (4) of the nucleotide sequence:

(A,G)TG(C,T)AA(C,T)AA(A,G,T)ATGCA(C,T) AACTT as shown in SEQ ID NO: 18 as a PCR primer corresponding to the C terminal sequence:

Lys-Leu-Cys-Ile-Leu-Leu-His.

By combining these two N terminal primers and the two C terminal primers, each of 4 primer sets, (1)+(3), (1)+(4), (2)+(3), or (2)+(4), was used to conduct PCR with cDNA from activated feline splenocytes as a template. PCR reaction was carried out with Amplitaq DNA polymerase (Takara Shuzo) for 35 cycles, each cycle consisting of 95° C. for 1 minute, 60° C. for 2 minutes and 72° C. for 2 minutes. The obtained PCR products were analyzed on 1% agarose gel. An amplified fragment of an expected size (600 bp) from the primer set (1)+(3) was detected. The DNA segment was excised from the gel and, using TA Cloning Kit (Invitrogen), cloned into pCRII vector contained in the kit.

In order to confirm that this DNA segment actually codes for the amino acid sequence of the feline IL12 p35 as reported by Bush et al., primers corresponding to SP6 promoter and T7 promoter region contained in this vector were used to produce amplified fragments for sequencing. As a result, this DNA segment proved to code for the identical amino acid sequence to the reported feline IL12 p35 ranging from the N terminal methionine to the C terminal histidine. Thus, this DNA segment was used for expression as described below.

Example 7

Co-expression of FLAF p40 and Feline IL12 p35 Genes

The cDNA of feline IL12 p35 obtained in Example 6 was cleaved from pCRII vector with restriction enzymes SacI and XhoI and the cleavage sites were blunt-ended with T4 DNA polymerase. pCAGn-mcs polyA vector was cleaved with a restriction enzyme SalI, the cleavage sites were blunt-ended with T4 DNA polymerase and the 5' terminal was dephosphorylated with bacterial alkaline phosphatase. To the resulting vector was ligated the above cDNA fragment of feline p35 with T4 ligase to construct an expression vector for feline IL12 p35 (CAGfIL12p35).

The thus prepared expression vector for feline IL12 p35 (CAGfIL12p35) alone (1 μg) or in combination with CAGfp40 (each 0.5 μg) were used to transfect COS7 cells using Lipofect Ace reagent and the procedures as described in Example 6. Each culture supernatant was measured for their activity to induce γ interferon to human PBMC but both failed to detect the activity (FIG. 12). That is, it was shown that a combination of the protein having the amino acid sequence of feline IL12 p35 as reported and the FLAF p40 protein did not exhibit the γ interferon inducing activity. The activity could not also be detected with cDNA of feline IL12 p35 alone. From this, it was possible that either (1) another molecule other than IL12 p35 is necessary for the activity, or (2) there may not be a full length amino acid sequence of feline IL12 p35 as reported by Bush et al.

As describe above, SDS-PAGE analysis in the presence of 2-mercaptoethanol of the gel filtration fractions having the γ interferon inducing activity revealed a band of molecular weight 35,000 as well as the unique main band of molecular weight 40,000 (FIG. 8). This protein of molecular weight 35,000 was referred to as "FLAF p35" and the N terminal was sequenced with 477A Protein Sequencer (Applied Bio Systems) as described for FLAF p40. The N terminal amino acid sequence of 10 amino acid residues was determined to be:

Arg-Asn-Leu-Pro-Thr-Pro-Thr-Pro-Ser-Pro as shown in SEQ ID NO: 19. In comparison with the N terminal amino acid sequence of feline IL12 p35 as reported by Bush et al., this amino acid sequence was completely identical. In this context, we considered that the feline IL12 p35 as reported by Bush et al. is defective for exerting the activity and thus cloned cDNA coding for the FLAF p35 molecule (FLAF p35 cDNA).

Example 8

Cloning of FLAF p35 Gene

FLAF p35 cDNA was cloned as described below. First, a whole RNA was prepared from feline splenocytes $3\times10^8$ (cultured in the presence of 0.01% PWM for 18 hours) in accordance with the protocol of ISOGEN reagent (Nippon Gene). Poly A+RNA was prepared from the whole RNA with polyA quick mRNA isolation kit (STRATAGENE). Feline splenocyte cDNA library was prepared from the poly A+RNA in accordance with the protocol of Uni-ZAP XR vector kit (STRATAGENE).

The PCR product coding for the feline IL12 p35 as described above was used as a probe for screening $2\times10^6$ plaques of the cDNA library as described in Maniatis et al., Molecular cloning, A Laboratory Manual 2 nd Ed., 8.46, Cold Spring Harbor Laboratory Press, N.Y., 1989 to give 3 positive plaques.

A whole nucleotide sequence of cDNA of these three plaques was determined to prove that a single clone (clone No. 20) had the amino acid sequence which was completely identical to the N terminal sequence of IL12 p35 (nucleotide sequence of clone No. 20 is described in SEQ ID NO: 8). When an open reading frame was determined for the nucleotide sequence of clone No. 20, coding regions for 25 amino acid residues, possibly a signal sequence, and for 197 amino acid residues were found. In comparison of this sequence with the reported amino acid sequence of feline IL12 p35, there were found difference in an amino acid residue at 2 sites and insertion of 3 amino acid residues within the signal sequence as well as 19 amino acid residues attached to the C terminal of feline IL12 p35 (FIG. 13). As such, it was shown that the protein encoded by FLAF p35 cDNA is a protein having a partially distinct amino acid sequence from that of feline IL12 p35. E. coli 92313 wherein plasmid (pFLAF20) comprising this clone No. 20 is incorporated has been deposited by the applicant in accordance with the Budapest Treaty under accession number FERM BP-5876 at National Institute of Bioscience and Human-Technology Agency of Industrial Science and Technology, 1–3, Higashi 1-chome, Tsukuba-shi, Ibaraki-ken, 305, Japan, on Mar. 14, 1997.

Example 9

Co-expression of FLAF p40 and FLAF p35

Figure 14:
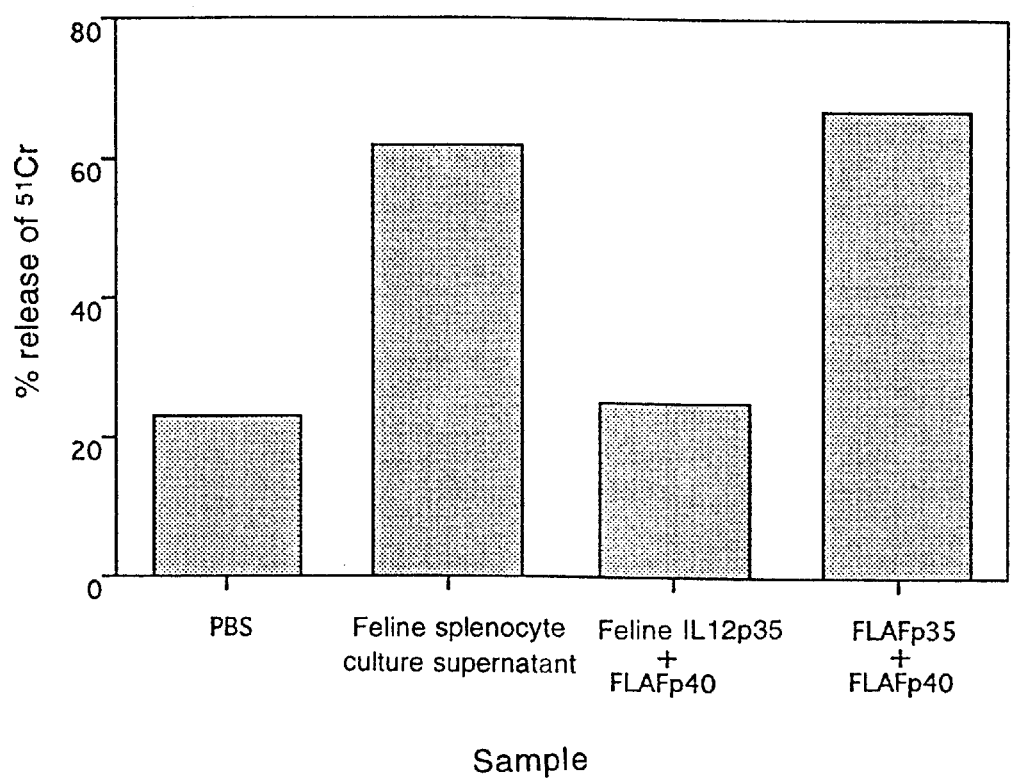
FIG. 14 shows that culture supernatant of COS cells incorporated with both FLAF p40 and FLAF p35 expression vectors exhibits the CTL enhancing activity equivalent to that of culture supernatant of feline splenocytes.

For expression of the obtained FLAF p35 cDNA in COS7 cells, the FLAF p35 cDNA was inserted into pCAGn-mcs polyA vector as described for FLAF p40 cDNA to construct an expression plasmid. First, the full length cDNA of FLAF p35 was cleaved from the clone No. 20 obtained herein- with restriction enzymes SacI and XhoI and the cleavage sites were blunt-ended with T4 DNA polymerase. The resulting cleaved DNA fragment was inserted into the SalI site of pCAGn-mcs polyA (after blunt-ending and dephosphorylation) to construct an expression plasmid. The thus prepared expression vector for FLAF p35 and the expression vector for FLAF p40 as described above were used to co-transfect COS7 cells using Lipofect Ace reagent as described in Example 6. The culture supernatant was recovered and measured for its activity to induce γ interferon to human PBMC, and as a result, the activity was detected in the culture supernatant (FIG. 12). Furthermore, the culture supernatant was also measured for its CTL enhancing activity in the human herpes virus system as described in Example 1, and as a result, the same CTL enhancing activity as found by the present inventors in the culture supernatant of feline splenocyte was detected (FIG. 14).

Thus, it was found that the FLAF p35 and p40 of the present invention in the form of a heterologous dimer exhibit the γ interferon inducing activity and the CTL enhancing activity, indicating that each cDNA for the FLAF p35 and p40 together encode a protein having the CTL enhancing activity as found by the present inventors in the culture supernatant of feline splenocyte. Furthermore, feline IL12 p35 as previously reported in the literatures could not exhibit the lymphocyte activating capacity even if it is co-expressed with the FLAF p40 found by the present inventors. This suggests that the FLAF activity requires not only the amino acid sequence of feline IL12 p35 as reported but also the addition-al sequence of 19 amino acid residues attached to the C terminal of feline IL12 p35 as mentioned above. Thus, the present inventors have found that said additional sequence of 19 amino acid residues is essential for exerting the CTL enhancing activity and the γ interferon inducing activity.

Example 10

Preparation of Transformants Which Stably Produce FLAF

Figure 15:
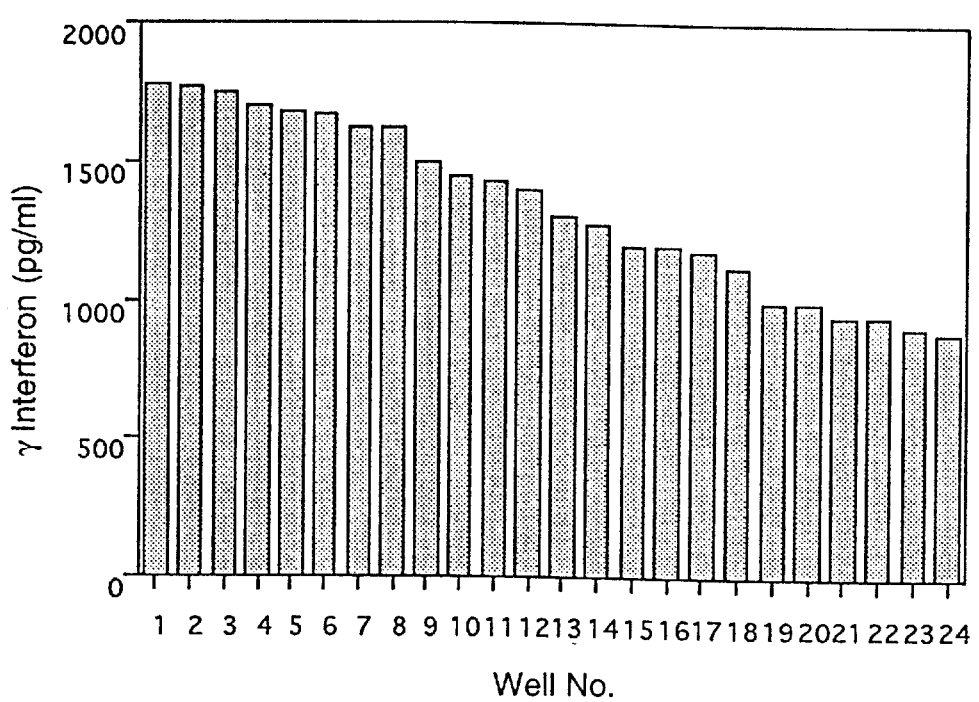
FIG. 15 shows that SFT34 cells incorporated with both FLAF p40 and FLAF p35 expression vectors stably produce FLAF at a clone level.

The results obtained with COS7 cells revealed that the feline lymphocyte activating factor is a heterologous dimer (FLAF) of peptides encoded by FLAF p35 and p40 cDNAs, respectively. However, since the expression with COS7 cells is merely transient, it is necessary to prepare cells which can stably produce FLAF for the purpose of preparing FLAF as a medicament. Thus, a stable transformant was prepared with SFT34 cells (Patent, International publication No. WO94/12658) derived from mouse myeloma as a host. The SFT34 cells can easily be suspended in a culture medium and quickly be adapted to a serum free culture medium. Each of FLAF p35 and p40 cDNAs was introduced into a CAG vector having G418 gene (Neo gene) as a selective marker. The vectors incorporating either FLAF p35 or p40 cDNAs were simultaneously introduced into the SFT34 cells with Lipofect Ace reagent. The cells were cultured on 10% FCS/RPMI medium containing 1 mg/ml G418 for 2 weeks to give G418 resistant SFT34 cells. The transformants were cloned by a limiting dilution procedure and those transformants which stably produced FLAF were obtained with the use of an index of the γ interferon inducing activity (FIG. 15). Culture supernatant (3 liters) of these clones was subjected to the purification procedures as described above. As a result, the obtained purified products exhibited the CTL enhancing activity and the γ interferon inducing activity like the FLAF purified from feline splenocytes, and thus, it became possible to stably obtain FLAF.

Example 11

Preparation of Antibody Against FLAF p40

A polyclonal antibody against FLAF p40 was prepared by injecting each 1 ml of the FLAF p40 expression plasmid (CAGfp40) (1 mg/ml; Example 5) intramuscularly into both rear legs of a rabbit four times at every 3 weeks. Western blot was used to determine whether the obtained antibody recognized FLAF p40 (FIG. 16). First, purified FLAF was subjected to SDS-PAGE in the absence of 2-mercaptoethanol and then transferred to PVDF membrane as described in Example 3. After the membrane was masked with 50 mM Tris-HCl (pH 8.0) supplemented with 5% skim milk, 150 mM NaCl, and 0.05% Tween 20 (TBST), it was incubated with serum from the rabbit administered with CAGfp40 diluted by 500 folds with TBST for 1 hour and then washed with TBST. Subsequently, the membrane was reacted with anti-rabbit IgG-HRP labeled antibody (Bio Rad) diluted by 2,000 folds with TBST at room temperature for 1 hour and, after washing, stained with Konica Immunostaining HRP 1000 (Konica K. K.) kit. As a result, it reacted with the FLAF p40 protein confirmed by the N terminal amino acid analysis. Furthermore, Western blot of the fractions obtained during purification of FLAF p40 with this antibody revealed that the fractions which reacted with the antibody overlapped with the fractions which exhibited the γ interferon inducing activity to ensure that the antibody can be used in the assay system of FLAF.

Example 12

Preparation of Monoclonal Antibody Against Partial Synthetic Peptide of FLAF p35

The amino acid sequence of FLAF p35 was analyzed for its hydrophilic and hydrophobic regions in accordance with Hopp et al. (T. P. Hopp et al., Proc. Natl. Acad. Sci. (USA), Vol. 78, 3824–3828, 1981). For the hydrophilic region, two peptides were prepared with a peptide synthesizer (Applied), each peptide having the sequence:

Thr-Ser-Glu-Glu-Ile-Asp-His-Glu-Asp-Ile-Thr-Lys-Asp-Lys-Thr-Ser-Thr-Val-Glu-Ala-Cys as shown in SEQ ID NO: 20 which corresponds to the amino acid residue Nos. 43 to 63 in the sequences of SEQ ID NOs: 3 and 4, and the sequence:

Ser-Ser-Leu-Glu-Glu-Pro-Asp-Phe-Tyr-Lys-Thr-Lys-Ile-Lys-Leu-Cys as shown in SEQ ID NO: 21 which corresponds to the amino acid residue Nos. 159 to 174 in the sequences of SEQ ID NOs: 3 and 4, respectively. Immunization with these two peptides is described below.

A group of gld mice of 6 weeks old (Nippon S L C K.K.) were used for immunization consisting of three intraperitoneal injections and one intravenous injection of the peptides. A synthetic peptide-KLH conjugate 100 μg was injected in the presence of complete Freund's adjuvant on Day 0, in the presence of incomplete Freund's adjuvant on Days 14 and 28, and in the absence of adjuvant on Day 42. Three days after the final immunization, splenocytes were harvested by the conventional procedures. Fusion of the splenocytes with myeloma cells p3X63Ag-8U1 was conducted in accordance with Kbhler and Milstein (Nature, 256, p495, 1975). A cell suspension after cell fusion was placed on a 96 well plate at 200 μl/well and the cells were cultured in an incubator containing 5% $CO_2$ at 37° C. for 24 hours. HT medium (normal medium supplemented with hypoxanthine $1\times10^{-4}$ M and thymidine $1.5\times10^{-3}$ M) was then added and the cells were cultured for additional 10 to 14 days. Among the culture supernatant from the wells where the fused cells grew to form colonies, a desired hybridoma was selected by the screening procedure as described below.

A desired hybridoma was selected by a combination of EIA and Western blot.

A primary screening by EIA is first described. The peptidic antigens as prepared above were immobilized on a 96 well plate at 2 μg/ml and the plate was masked with a 1% solution of bovine serum albumin. The plate was added with the culture supernatant of the hybridomas obtained by cell fusion, incubated at 4° C. for 2 hours and washed with 0.1% Tween 20/PBS three times. The plate was added with a solution of an anti-mouse immunoglobulin antibody labeled with peroxidase (Kappel; diluted by 5,000 folds; 100 μl), incubated at 4° C. for 1 hour and washed with 0.1% Tween 20/PBS three times. Subsequently, a TMBZ substrate solution was added to develop in the usual manner and an absorbance at 450 nm was measured. The thus selected wells which reacted with the synthetic peptides were subjected to a secondary screening with Western blot.

The purified FLAF was subjected to SDS-PAGE in the absence of 2-mercaptoethanol and then transferred to PVDF membrane as described in Example 11. The membrane was masked, added with the culture supernatant which tested positive in the EIA screening to react at room temperature for 1 hour and washed with TBST. The membrane was then reacted with an anti-mouse IgG-HRP labeled antibody (Bio Rad; diluted by 2,000 folds) at room temperature for 1 hour and, after washing, stained with Konica Immunostaining HRP 1000 kit (Konica K.K.). As a result, a specific reaction with FLAF was observed for the antibodies produced by the hybridomas from 4 clones (F6-13, F6-15, F6-17 and F6-18) obtained by immunization with the synthetic peptide of SEQ ID NO: 20 and from 3 clones (F18-2, F18-4 and F18-18) obtained by immunization with the synthetic peptide of SEQ ID NO: 21. Among these clones, the hybridomas F6-13 and F18-4 have been deposited in accordance with the Budapest Treaty under accession numbers FERM BP-5924 and FERM BP-5925, respectively, at National Institute of Bioscience and Human-Technology Agency of Industrial Science and Technology, 1-3, Higashi 1-chome, Tsukuba-shi, Ibaraki-ken, 305, Japan, on Apr. 18, 1997.

Western blot of the fractions obtained during purification of FLAF with the culture supernatant from these 7 clones revealed that the fractions which reacted with these antibodies overlapped with the fractions which exhibited the γ interferon inducing activity to ensure that these antibodies can be used in the assay system of FLAF.

Then, a gel with an immobilized antibody was prepared by immobilizing the antibody (subtype IgG1) obtained from, for example, the clone F18-4 on a CNBr-activated Sepharose (Pharmacia) in accordance with the protocol of Pharmacia. The gel (1 ml) was equilibrated with 10 mM phosphate (pH 7.0)-100 mM NaCl buffer. To the gel was applied a crude FLAF (10 ml) dialyzed against the same buffer. After washing with the same buffer, elution was carried out with 0.1 M glycine HCl buffer (pH 3.0). As a result, a high purity of FLAF was detected in the eluted fractions to prove that the gel with the immobilized monoclonal antibody can be used for purification of FLAF.

Example 13

Effect of FLAF for Ameliorating Feline Herpes Virus (FHV) Infection in Cats

Figure 17:
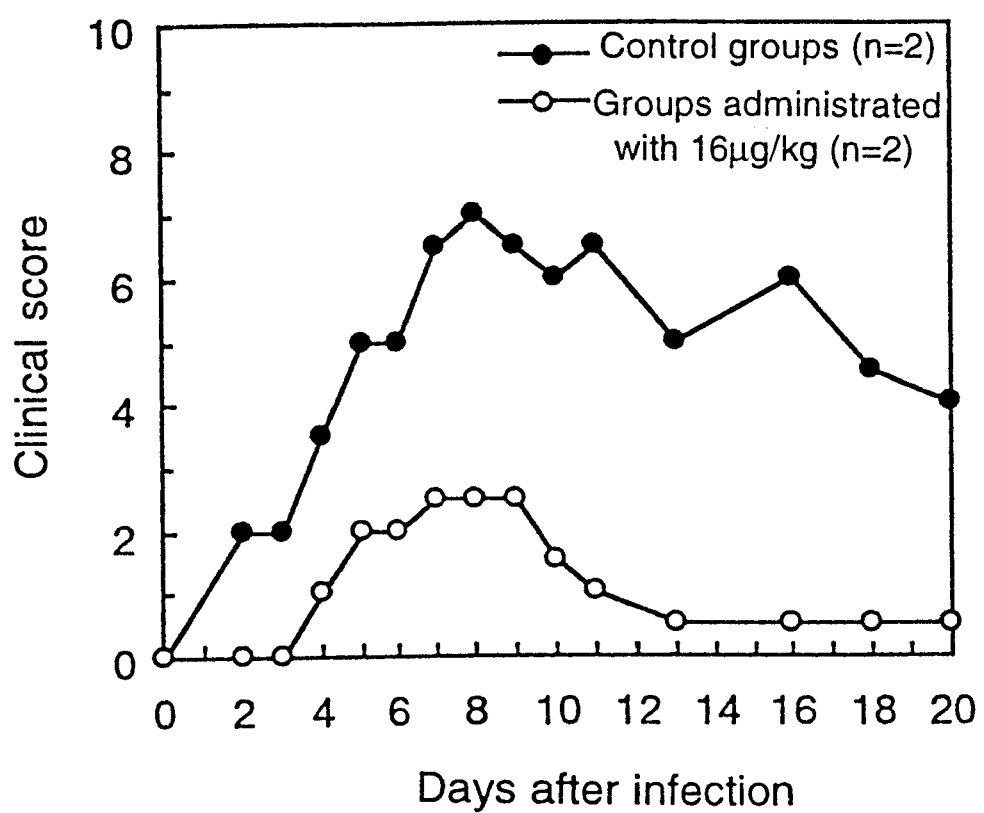
FIG. 17 shows an efficacy of FLAF for treating cats infected with feline herpes virus wherein the axis of abscissas depicts days after compulsory infection, the axis of ordinates depicts a total of clinical score and "In" means a number of animals per group.

Conventional cats obtained from the Animal Control Center of Kumamoto Prefecture were tested for an anti-FHV antibody titer after bleeding and those cats tested negative for the anti-FHV antibody titer were used in this experiment. The cats weighing 1 to 2.5 kg were compulsorily infected nasally with FHV-1-K1 strain at $10^5$ $TCID_{50}$. On days 2, 4 and 6 after the compulsory infection, the purified FLAF at 16 µg/kg was intravenously administered via the jugular vein. A control group (2 animals) received a physiological saline by an intravenous administration via the jugular vein with the same schedule. The cats were observed for their clinical conditions such as tears, conjunctivitis, rhinorrhea, sneeze, slaver and ulcer at the nose edge were observed with the lapse of time and scored as 0 for no symptom, 1 through 3 for symptoms of various severity. FIG. 17 shows cumulative scores obtained by observation with the lapse of time. As a result, the clinical conditions were remedied in the group administered with FLAF as compared to the control group, showing that FLAF is effective for treating FHV infectious diseases in vivo. In addition, after administration of FLAF, no side effect such as fever, diarrhea, vomiting or another shock-like symptom was observed. Thus, FLAF can be applied as treating agents effective against FHV infectious diseases with no side effect.

Example 14

Enhancement of Recombinant FLAF Expression with Animal Cells as a Host by Modification of FLAF p35 cDNA As described in Example 9, FLAF having the biological activity can be obtained by co-transfecting animal cells with the expression plasmids wherein either FLAF p40 or p35 cDNA was incorporated. However, this procedures can only provide FLAF at as low as several µg/l. In order to improve the production rate, the FLAF p35 cDNA was modified as described below.

Step 1

First, using the plasmid pFLAF20 obtained in Example 8 as a template, PCR reaction was carried out with Amplitaq DNA polymerase (Takara Shuzo K.K.) for 35 cycles, each cycle consisting of 95° C. for 1 minute, 60° C. for 2 minutes and 72° C. for 2 minutes, using a synthetic primer having the sequence of SEQ ID NO: 22 corresponding to the amino acid sequence ranging from the amino acid residues No. −25 to No. −3 as shown in SEQ ID NO: 3 and a synthetic primer having the sequence of SEQ ID NO: 23 corresponding to the 3' poly A sequence of FLAF p35 cDNA. The primer having the sequence of SEQ ID NO: 22 comprises Kozak sequence (J. Cell. Biol., Vol. 108, 229–233, 1989) which is reported to enhance the translation efficiency at its N terminal. The obtained DNA fragments were digested with restriction enzymes SacI and XhoI and subcloned into the vector pBluescript which has previously been digested with the same enzymes.

Step 2

For the insertion region of the plasmid obtained in Step 1, a nucleotide sequence of a region coding for an amino acid was determined to confirm that no mutation such as a frame shift occurred. Among the amino acid residues in the coding region, Nos. 64, 68 and 124 leucine (Leu) as shown in SEQ ID NO: 3 are coded by the codon TTA. Among six codons used for encoding Leu, TTA is the least used in an animal cell (Current Protocols in Molecular Biology, Supplement 12 A.1.9.). Thus, this codon used for Leu at the three positions was replaced with CTG. First, there were prepared a synthetic DNA as shown in SEQ ID NO: 24 corresponding to the sequence in the vicinity of the restriction enzyme site EcoRV site and a synthetic DNA as shown in SEQ ID NO: 25 corresponding to the sequence in the vicinity of the restriction enzyme site BamHI site. Using these two synthetic DNAs as a primer, PCR reaction was carried out using the DNA obtained in Step 1 as a template under the conditions as described in Step 1. The DNA fragment amplified by this reaction was subjected to an agarose gel electrophoresis to resolve impurities and recovered from the gel. The DNA fragment was digested with BamHI and EcoRV and the obtained BamHI-EcoRV fragment was inserted into the BamHI-EcoRV site of the plasmid obtained in Step 1. A nucleotide sequence of the DNA fragment inserted in the plasmid was determined to confirm that no mutation such as a frame shift occurred.

Then, the plasmid was digested with restriction enzymes SacI and BsmAI so that the plasmid was cleaved at the SacI site situated just upstream of Kozak sequence and at the BsmAI site situated just downstream of the termination codon to produce a fragment of about 800 bp comprising a full length of the coding region of FLAF p35. The resulting fragment was blunt-ended with T4 DNA polymerase (a nucleotide sequence of this fragment is shown in SEQ ID NO: 26). This DNA fragment was inserted into the expression vector pCAGn-mcs, which has previously been digested with SalI and blunt-ended with T4 DNA polymerase, to construct a novel FLAF p35 expression plasmid (referred to as CAGfp35V2).

Both CAGfp35V2 and CAGfp40 as described in Example 5 were simultaneously introduced into SFT cells as described in Example 10 to prepare a stable transformant. Each 2 liter sample of this stable transformant and the stable transformant obtained in Example 10 were cultured. Each culture supernatant was purified as described in Example 2 and using the gel with the immobilized monoclonal antibody against the synthetic peptide of FLAF p35 as described in Example 12. As a result, the culture supernatant obtained from the transformant with CAGfp35V2 could provide purified FLAF at a higher amount by 200 folds than the culture supernatant obtained from the transformant with CAGfp35.

Figure 18:
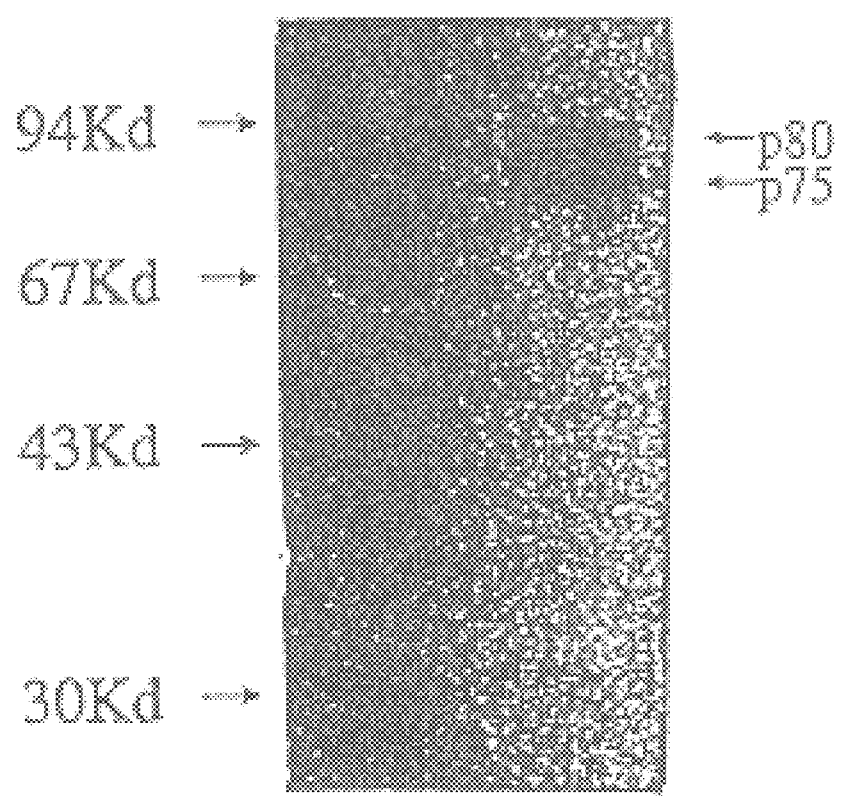
FIG. 18 is a photograph showing the results of sodium dodecyl sulfate polyacrylamide gel electrophoresis (SDS-PAGE) of purified FLAF in the absence of 2-mercaptoethanol wherein the gel is dyed with Coomassie Brilliant Blue.

The purified FLAF was subjected to SDS-PAGE in the absence of 2-mercaptoethanol to prove two bands of MW 75,000 (referred to as p75) and MW 80,000 (referred to as p80) as shown in FIG. 18. These bands were analyzed by Western blot as described in Example 2 wherein two membranes were prepared, i.e. one using a monoclonal antibody against the partial synthetic peptide of FLAF p35 produced by the clone F18-4 as described in Example 12 as a primary antibody and another using the antibody against FLAF p40 as described in Example 11. As a result, both p75 and p80 reacted with both antibodies to confirm that they are both heterologous dimer of FLAF p35 and FLAF p40.

In order to investigate the biological activity of p75 and p80, the activity to induce γ interferon against human PBMC was measured as described in Example 1. Resolution of p75 and p80 was carried out as described below. The purified FLAF was subjected to SDS-PAGE in the absence of 2-mercaptoethanol, the gel was stained with Kappa Stain Kit (Bio Rad) and each gel comprising the bands of p75 and p80 was excised. These gels were separately covered in a dialysis tube, thereto was added 200 μl of 25 mM Tris, 192 mM glycine buffer, and electricity was charged using an electrophoretic bath filled with the same buffer at 50 volts for 1 hour. FLAF eluted out of the gel into the dialysis tube was dialyzed against PBS. The obtained sample was tested for the activity to induce γ interferon against human PBMC using PBS as a control.

Figure 19:
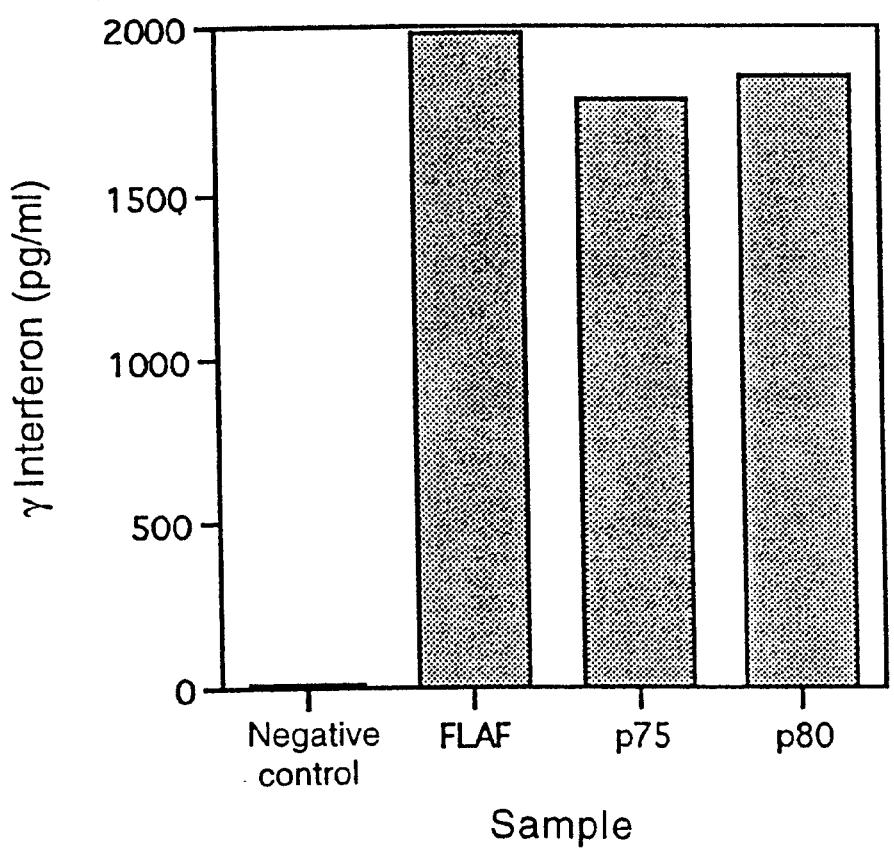
FIG. 19 shows the γ interferon inducing activity of p75, p80 and purified FLAF extracted from the gel wherein PBS is used as a negative control.

As a result, both p75 and p80 exhibited the γ interferon inducing activity as shown in FIG. 19.

Reference Example

Cloning of FLAF p35 and p40 cDNAs using Human IL12 α Chain and β Chain cDNAs as a Probe It was confirmed that the FLAF p35 and p40 obtained herein had a high homology with human IL12 α chain and β chain as a result of homology search for their nucleotide sequence with the known data base (for example, GenBank, SWISS-PROT etc.). Cloning of FLAF p35 and FLAF p40 cDNAs is described in Examples 4 and 8, respectively. However, these procedures are not only quite cumbersome but also provide a positive clone only at a quite low rate. Thus, in order to clone FLAF p35 and p40 cDNAs more efficiently, human IL12 α chain and β chain cDNAs were cloned by using PCR and, using these human IL12 cDNAs as a probe, the cDNA library prepared as described in Example 4 was screened. As a result, one FLAF p35 cDNA and two FLAF p40 cDNAs were detected among $2 \times 10^6$ plaques. A nucleotide sequence of these clones was determined to be completely identical to the sequences of SEQ ID NOs: 5 and 8. Thus, it was found that FLAF p35 and FLAF p40 cDNAs could easily be cloned by using human IL12 α chain and β chain cDNAs as a probe.

What is claimed is:

1. A DNA having a nucleotide sequence coding for
   (1) a feline IL12 p40 polypeptide having the amino acid sequence as shown in SEQ ID NO:1, SEQ ID NO:1 with deletion, insertion or substitution at any one to several amino acid residues; SEQ ID NO:2; or SEQ ID NO:2 with deletion, insertion or substitution at any one to several amino acid residues; or a portion of the amino acid sequence as shown in SEQ ID NO:1; or any of foregoing polypeptides that is a recombinant polypeptide prepared by using a genetic recombination technique; or
   (2) a feline IL12 p35 polypeptide having the amino acid sequence as shown in SEQ ID NO:3; SEQ ID NO:3 with deletion, insertion or substitution at any one to several amino acid residues wherein the C-terminal amino acid sequence is Ala-Phe-Arg-Ile-Arg-Ala-Val-Thr-Ile-Asn-Arg-Met-Met-Ser-Tyr-Leu-Asn-Ser-Ser as shown in SEQ ID NO:10; SEQ ID NO:4; SEQ ID NO:4 with deletion, insertion or substitution at any one to several amino acid residues wherein the C-terminal amino acid sequence is Ala-Phe-Arg-Ile-Arg-Ala-Val-Thr-Ile-Asn-Arg-Met-Met-Ser-Tyr-Leu-Asn-Ser-Ser as shown in SEQ ID NO:10; or a portion of the amino acid sequence as shown in SEQ ID NO:3; or any of foregoing polypeptides that is a recombinant polypeptide prepared by using a genetic recombination technique; or
   (3) a protein of a homologous dimer of any of the polypeptides in the group (1); or
   (4) a protein of a homologous dimer of any of the polypeptides in the group (2); or
   (5) a protein of a heterologous dimer of any of the polypeptides in the group (1) with any of the polypeptides in the group (2).

2. The DNA of claim 1 coding for a said protein having an activity of activating lymphocytes.

3. The DNA of claim 2, wherein the lymphocytes are feline lymphocytes.

4. The DNA of claim 2, wherein the lymphocytes are cytotoxic T lymphocytes.

5. The DNA of claim 1 which comprises the nucleotide sequence as shown in SEQ ID NO:5 encoding a feline IL12 p40 polypeptide.

6. The DNA of claim 1 which comprises the nucleotide sequence as shown in SEQ ID NO:6 encoding a feline IL12 p40 polypeptide.

7. The DNA of claim 1 which comprises the nucleotide sequence as shown in SEQ ID NO:7 encoding a feline IL12 p40 polypeptide.

8. The DNA of claim 1 which comprises the nucleotide sequence as shown in SEQ ID NO:8 encoding a feline IL12 p35 polypeptide.

9. The DNA of claim 1 which comprises the nucleotide sequence as shown in SEQ ID NO:9 encoding a feline IL12 p35 polypeptide.

10. The DNA of claim 1 which comprises the nucleotide sequence as shown in SEQ ID NO:26 encoding a feline IL12 p35 polypeptide.

11. The DNA of claim 1 which comprises a portion of the nucleotide sequence as shown in SEQ ID NO:5.

12. A DNA which hybridizes with a DNA having a nucleotide sequence complementary to the nucleotide sequence as shown any of SEQ ID No. 5 to 9 and which codes for a protein having the activity to activate feline lymphocytes.

13. A recombinant DNA molecule comprising the DNA as set forth in claim 1.

14. The recombinant DNA molecule of claim 13, wherein the vector moiety constituting said recombinant DNA molecule is selected from plasmid, viral vector or cosmid.

15. A transformant which is transformed with a DNA as set forth in claim 1.

16. The transformant of claim 15 which is a host selected from *E. coli*, yeast, an insect cell, an animal cell or a plant cell.

17. A process for preparing a polypeptide or a protein, comprising culturing a transformant according to claim 15 so that said transformant produces said polypeptide or said protein, and purifying said polypeptide or said protein.

* * * * *

UNITED STATES PATENT AND TRADEMARK OFFICE
CERTIFICATE OF CORRECTION

PATENT NO.    : 6,518,045 B1
DATED         : February 11, 2003
INVENTOR(S)   : Takayuki Imamura et al.

It is certified that error appears in the above-identified patent and that said Letters Patent is hereby corrected as shown below:

Column 9,
Line 17, delete "PLAF" and insert therefor -- FLAF --;
Line 46, delete "1x10/ml" and insert therefor -- $1x10^6$/ml --:

Column 10,
Line 42, delete "1x10/ml" and insert therefor -- $1x10^6$/ml -- :
Line 56, delete "PLAFp40" and insert therefor -- FLAFp40 --;

Column 14,
Line 42, delete "pbluescript" and insert therefor -- pBluescript --;

Column 15,
Line 29, delete "cAGf40" and insert therefor -- CAGf40 --.

Signed and Sealed this

Twenty-second Day of July, 2003

JAMES E. ROGAN
*Director of the United States Patent and Trademark Office*